(12) United States Patent
Lindsey et al.

(10) Patent No.: US 6,642,376 B2
(45) Date of Patent: Nov. 4, 2003

(54) RATIONAL SYNTHESIS OF HETEROLEPTIC LANTHANIDE SANDWICH COORDINATION COMPLEXES

(75) Inventors: Jonathan S. Lindsey, Raleigh, NC (US); Thoralf Gross, Bad Doberan (DE)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/135,220

(22) Filed: Apr. 29, 2002

(65) Prior Publication Data

US 2003/0092896 A1 May 15, 2003

Related U.S. Application Data

(60) Provisional application No. 60/287,723, filed on Apr. 30, 2001.

(51) Int. Cl.$^7$ .................... C07D 205/00; C07D 487/22; G11C 13/00; C07F 5/00
(52) U.S. Cl. .................... 540/201; 540/145; 534/15; 556/1; 365/106; 365/151; 365/153; 365/173
(58) Field of Search .................... 540/145, 201; 365/106, 151, 153, 173; 534/15; 556/1

(56) References Cited

U.S. PATENT DOCUMENTS 6,212,093 B1    4/2001   Lindsey ..................... 365/151

OTHER PUBLICATIONS

Radzki et al., Inorganica Chimica Acta, vol. 205, No. 2, pp. 213–219 (1993).*
Aspinall, Helen C., et al., *Preparation of the Bis(trimethylsilyl)amido Lanthanide Chlorides [{Ln[N(SiMe$_3$)$_2$]$_2$(μ–CL)(thf)}$_2$] (thf=tetrahydrofuran), and the Crystal and Molecular Structures of the Gadolinium and Ytterbium Complexes,* J. Chem. Socl, Dalton Trans., pp. 623–626 (1989).
Chabach, Driss, et al., *Mixed–Metal Triple–Decker Sandwich Complexes with the Porphyrin/Phthalocyanine/Porphyrin Ligand System,* Angew. Chem. Int. Ed. Engl., vol. 35, No. 8, pp. 898–899 (1996).
Wong, Ching–Ping, *[5,10,15,20–Tetraphenylporphyrinato(2–)] Lanthanides and Some [5,10,15,20–Tetraphenylporphyrinato(2–)] Actinides,* Inorg. Synth., vol. 22, pp. 156–162 (1983).
Wong, Wai–Kwok, et al., *Synthesis and crystal structures of cationic lanthanide(III) monoporphyrinate complexes,* J. Chem. Soc., Dalton Trans., pp. 615–622 (1999).

* cited by examiner

*Primary Examiner*—Porfirio Nazario-Gonzalez
(74) *Attorney, Agent, or Firm*—Myers Bigel Sibley & Sajovec

(57) ABSTRACT

A half-sandwich coordination complex, useful for the synthesis of triple-decker sandwich coordination compounds, is produced by reacting a precursor complex of the formula XM(R$^1$)$_2$ wherein X is a halogen, M is a metal, and R$^1$ is an amide, with a free base porphyrinic macrocycle to produce said half-sandwich complex. The half-sandwich coordination complex can be used to make a triple-decker sandwich coordination compound by reacting a half-sandwich coordination complex as described above with a double-decker sandwich coordination compound.

31 Claims, No Drawings

RATIONAL SYNTHESIS OF HETEROLEPTIC LANTHANIDE SANDWICH COORDINATION COMPLEXES

RELATED APPLICATIONS

This application claims the benefit of Provisional Application Ser. No. 60/287,723, filed Apr. 30, 2001, the disclosure of which is incorporated by reference herein in its entirety.

FIELD OF THE INVENTION

The present invention concerns methods of making triple decker sandwich coordination compounds and intermediates useful for carrying out such methods.

BACKGROUND OF THE INVENTION

The storage of information at the molecular level can afford extraordinarily high memory densities. An approach toward molecular-based information storage that involves the storage of data in distinct molecular oxidation states has been developed. (see, e.g., Lindsey, U.S. Pat. No. 6,212,093; Roth, et al. (2000) *J. Vac. Sci. Technol. B* 18:2359–2364; Gryko, et al. (2000) *J. Org Chem.* 65:7345–7355; Gryko, et al. (2000) *J. Org. Chem.* 65:7356–7362; Clausen, et al. (2000) *J. Org. Chem.* 65:7363–7370; Clausen, et al. (2000) *J. Org Chem.* 65:7371–7378; Li, et al. (2000) *J. Org. Chem.* 65:7379–7390; Gryko, et al. (2001) *J. Mater. Chem.* 11: 1162–1180). Thiol-derivatized redox-active molecules are attached to an electroactive surface, thereby enabling reading and writing to be achieved via electrical methods (Roth, et al. *Anal. Chem.* submitted). The information storage density can be increased commensurate with the number of available oxidation states of the molecules in a memory storage location.

Among the various classes of molecules examined for information storage, (Gryko, et al. (2000) *J. Org. Chem.* 65:7345–7355; Gryko, et al. (2000) *J. Org. Chem.* 65:7356–7362; Clausen, et al. (2000) *J. Org. Chem.* 65:7363–7370; Clausen, et al. (2000) *J. Org. Chem.* 65:7371–7378) the triple-decker lanthanide sandwich molecules (Tran-Thi, T. -H. (1997) *Coord. Chem. Rev.* 160:53–91; Ng and Jiang (1997) *Chem. Soc. Rev.* 26:433–442) comprised of porphyrinic ligands proved most attractive due to their large number of redox states, reversible electrochemistry, and relatively low oxidation potentials. The triple deckers generally exhibit four oxidation states in the range 0–1.4 V (vs Ag/Ag$^+$), corresponding to the formation of the monocation, dication, trication, and tetracation (Li, et al. (2000) *J. Org. Chem.* 65:7379–7390; Gryko, et al. (2001) *J. Mater. Chem.* 11: 1162–1180). A further attraction of this class of molecules stems from the possibility of interleaving the potentials of two triple deckers, thereby achieving as many as eight accessible cationic oxidation states. This approach for molecular-information storage requires the ability to synthesize triple deckers of a given type bearing linkers for attachment to an electroactive surface.

The synthesis of homoleptic porphyrin triple deckers, first reported by the groups of Buchler (Buchler and Knoff (1985) In: *Optical Properties and Structure of Tetrapyrroles;* Blauer, G.; Sund, H., Eds.; de Gruyter: Berlin, pp 91–105) and Weiss (Buchler, et al. (1986) *J. Am. Chem. Soc.* 108:3652–3659), employed the reaction of a lanthanide acetylacetonate complex with a porphyrin in refluxing 1,2, 4-trichlorobenzene (1,2,4-trichlorobenzene has bp 214° C.; the oil bath temperature for these reactions was set at ~230° C.). This procedure grew out of a method developed by Horrocks for the preparation of (Por)M(acac) complexes by reaction of a porphyrin with a lanthanide(acac) complex in refluxing 1,2,4-trichlorobenzene (Wong, et al. (1974) *J. Am. Chem. Soc.* 96:7149–7150; Wong, C. -P. (1983) *Inorg. Synth.* 22:156–162). The synthesis of heteroleptic (porphyrin/phthalocyanine) triple deckers has been achieved by two distinct procedures, an undirected "reaction-of-monomers" route and a directed "monomer+dimer" route (vide infra). The former route proceeds as follows: A porphyrin is treated with excess M(acac)$_3$.nH$_2$O in refluxing 1,2,4-trichlorobenzene, affording the porphyrin.M(acac) complex (Moussavi, et al. (1986) *Inorg. Chem.* 25:2107–2108). The mixture is then treated with a dilithium phthalocyanine under continued reflux. In various applications of this method it has become clear that the product composition depends on the lanthanide, the nature of the substituents on the porphyrin and phthalocyanine, and the ratio of the reactants (Ng and Jiang (1997) *Chem. Soc. Rev.* 26:433–442). In our hands, the reaction-of-monomers route using M=Eu afforded two double deckers of composition (Por)M(Pc) and (Pc)M(Pc), and three triple decker complexes of composition (Por)M(Pc)M(Por), (Pc)M(Por)M (Pc), and (Pc)M(Pc)M(Por); the yields of the three types of triple deckers were typically 10–20%, <3%, and 10–14%, respectively, upon chromatographic purification (Li, et al. (2000) *J. Org. Chem.* 65:7379–7390).

Accordingly, there remains a need for new methods for the rational synthesis of heteroleptic lanthanide sandwich coordination complexes.

SUMMARY OF THE INVENTION

A first aspect of the present invention is a half-sandwich coordination complex, useful for the synthesis of triple-decker sandwich coordination compounds, produced by the process of: reacting a precursor complex of the formula XM(R$^1$)$_2$ with a free base porphyrinic macrocycle to produce said half-sandwich complex, wherein X is a halogen, M is a metal (e.g., a metal selected from the group consisting of Ce, Pr, Nd, Sm, Eu, Gd, Tb, Dy, Ho, Er, Tm, Yb and Lu), and R$^1$ is an amide.

The precursor complex may be produced by reacting a compound of the formula MX$_3$, wherein M is a lanthanide metal and X is halogen, with a compound of the formula ZR$^1$, wherein Z is a counter-ion and R$^1$ is an amide, to produce the precursor complex of the formula X-M(R$^1$)$_2$.

Alternatively stated, the present invention provides a half-sandwich coordination complex, useful for the synthesis of triple-decker sandwich coordination compounds, according to Formula (I):

$$\text{L-M-X} \qquad\qquad\qquad\qquad\qquad (I)$$

wherein X is a halogen; M is a metal (e.g., a metal selected from the group consisting of Ce, Pr, Nd, Sm, Eu, Gd, Tb, Dy, Ho, Er, Tm, Yb and Lu), and L is a porphyrinic macrocycle group.

A further aspect of the present invention is a method of making a half sandwich coordination complex, comprising the steps of: reacting a precursor complex of the formula X-M(R$^1$)$_2$, with a free base porphyrinic macrocycle to produce said half-sandwich complex; wherein X is a halogen, M is a metal (e.g., a metal selected from the group consisting of Ce, Pr, Nd, Sm, Eu, Gd, Tb, Dy, Ho, Er, Tm, Yb and Lu), and R$^1$ is an amide.

A further aspect of the present invention is a method of making a triple-decker sandwich coordination compound, comprising the step of reacting a half-sandwich coordination complex as described above with a double-decker sandwich coordination compound, preferably in a polar aprotic solvent, and preferably at a temperature of at least 100° C., to produce said triple-decker sandwich coordination compound.

The foregoing and other objects and aspects of the present invention are explained in greater detail below.

DETAILED DESCRIPTION OF THE PREFERRED EMBODIMENTS

The terms "sandwich coordination compound" or "sandwich coordination complex" refer to a compound of the formula $L^n M^{n-1}$, where each L is a heterocyclic ligand (as described below), each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand. Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another). See, e.g., D. Ng and J. Jiang, Sandwich-type heteroleptic phthalocyaninato and porphyrinato metal complexes, *Chem. Soc. Rev.* 26, 433–442 (1997).

The term "double-decker sandwich coordination compound" refers to a sandwich coordination compound as described above where n is 2, thus having the formula $L^1\text{-}M^1\text{-}L^2$, wherein each of $L^1$ and $L^2$ may be the same or different. See, e.g., J. Jiang et al., Double-decker Yttrium (III) Complexes with Phthalocyaninato and Porphyrinato Ligands, *J. Porphyrins Phthalocyanines* 3: 322–328 (1999).

The term "triple-decker sandwich coordination compound" refers to a sandwich coordination compound as described above where n is 3, thus having the formula $L^1\text{-}M^1\text{-}L^2\text{-}M^2\text{-}L^3$, wherein each of $L^1$, $L^2$ and $L^3$ may be the same or different, and $M^1$ and $M^2$ may be the same or different. See, e.g., D. Arnold et al., Mixed Phthalocyaninato-Porphyrinato Europium(III) Triple-decker Sandwich Complexes Containing a Conjugated Dimeric Porphyrin Ligand, *Chem. Lett.* 6: 483–484 (1999).

The term "homoleptic sandwich coordination compound" refers to a sandwich coordination compound as described above wherein all of the ligands L are the same.

The term "heteroleptic sandwich coordination compound" refers to a sandwich coordination compound as described above wherein at least one ligand L is different from the other ligands therein.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring (e.g., a pyrrole ring).

The term porphyrin refers to a cyclic structure typically composed of four pyrrole rings together with four nitrogen atoms and two replaceable hydrogens for which various metal atoms can readily be substituted. A typical porphyrin is hemin.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl, while acting as substituent can itself have additional substituents (e.g., the substituents provided for $S^n$ in the various formulas herein).

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2$CH—).

The term "halogen" refers to one of the electronegative elements of group VIIA of the periodic table (fluorine, chlorine, bromine, iodine, astatine).

The term "nitro" refers to an —$NO_2$ group.

The term "amino" refers to an —$NH_2$ group.

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "cyano" refers to a —CN group.

The term "thiocyanato" refers to an —SCN group.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples include, but are not limited to acetyl, benzoyl, etc.

In preferred embodiments, when a metal is designated by "M" or "M$^n$", where n is an integer, it is recognized that the metal may be associated with a counterion.

The term "substituent" as used in the formulas herein, particularly designated by S or S$^n$ where n is an integer, in a preferred embodiment refer to redox-active groups (subunits) that can be used to adjust the redox potential(s) of the subject compound. Preferred substituents include, but are not limited to, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In preferred embodiments, a substituted aryl group is attached to a porphyrin or a porphyrinic macrocycle, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl.

All United States patent references cited herein are to be incorporated by reference herein in their entirety.

Porphyrinic macrocycles as described above are known. Particular examples are given in U.S. Pat. No. 6,212,093 to Lindsey. Porphyrinic macrocycles may be converted to free base form in accordance with standard techniques for the displacement of coordinating metals. Examples of suitable porphyrinic macrocycles include but are not limited to compounds of Formula X and compounds of Formula XI:

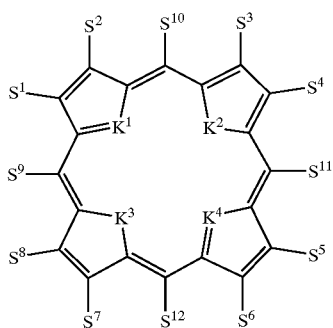

(X)

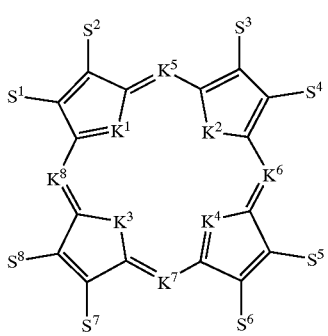

(XI)

wherein:
$K^1$, $K^2$, $K^3$, $K^4$, $K^5$, $K^6$, $K^7$, and $K^8$ are independently selected from the group consisting of N, O, S, Se, and Te (preferably N); and
$S^1$, $S^2$, $S^3$, $S^4$, $S^5$, $S^6$, $S^7$, $S^8$, $S^9$, $S^{10}$, $S^{11}$, and $S^{12}$ are independently selected substituents each selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

In addition, each pair of $S^1$ and $S^2$, $S^3$ and $S^4$, $S^5$ and $S^6$, and $S^7$ and $S^8$, may independently form an annulated arene (e.g., selected from the group consisting of benzene, naphthalene, and anthracene), which annulated arene may in turn may be unsubstituted or (e.g., substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl).

Metals "M" used to carry out the present invention are, in general, lanthanides such as Ce, Pr, Nd, Sm, Eu, Gd, Tb, Dy, Ho, Er, Tm, Yb or Lu (preferably Ce, Pr, Nd, Sm, or Eu, and most preferably Ce or Eu).

Precursor complexes of the formula $XM(R^1)_2$ used to carry out the present invention may be produced by reacting a compound of the formula $MX_3$, wherein M is a lanthanide metal and X is halogen, with a compound of the formula $ZR^1$, wherein Z is a counter-ion and $R^1$ is an amide, to produce the precursor complex of the formula $X-M(R^1)_2$. Suitable amides $R^1$ are generally of the formula $NR^2R^3$, wherein $R^1$ and $R^3$ are each independently selected from the group consisting of $C_1$–$C_6$ alkyl, and silyl. Particularly prefered are disilylamides such as —$N(SiMe_3)_2$. Any suitable counterion may be employed, including but not limited to Cl, Br, and I. The reaction may be carried out with the same solvents as described below (e.g., glyme solvents), and may be carried out at any suitable temperature, such as room temperature or 0° C.

A half sandwich coordination complex of the present invention is made by reacting a precursor complex of the formula $X-M(R^1)_2$ with a free base porphyrinic macrocycle to produce said half-sandwich complex. In general, and as described above, X is a halogen, M is a metal (e.g., a metal selected from the group consisting of Ce, Pr, Nd, Sm, Eu, Gd, Tb, Dy, Ho, Er, Tm, Yb and Lu), and $R^1$ is an amide. The reaction may be carried out in any suitable organic solvent (generally polar), but is typically carried out in a nonaqueous solvent, and is preferably carried out in a polar aprotic organic solvent. Particularly suitable are glyme solvents (solvents comprising multiple alkyl ether units, and generally having a boiling point between 100° C. and 200° C.), such as bis(2-methoxyethyl) ether. The reacting step may be carried out at any suitable temperature, but is preferably carried out at a temperature of at least 100° C., and is preferably carried out at a temperature of 200° C. or less. The reaction may be carried out in an inert atmosphere, may be carried out under standard dry conditions, and may be carried out in any suitable apparatus such as a Schlenk apparatus.

Without wishing to be bound to any particular theory of the invention, it is believed the foregoing process provides a half-sandwich coordination complex according to Formula (I):

L-M-X (I)

wherein X is a halogen; M is a metal and L is a porphyrinic macrocycle group as described above. Of course, this is an intermediate compound, and the particular structure of this compound is not critical to carrying out methods of synthesizing the triple-decker compounds described herein.

The half-sandwich coordination complexes synthesized as described above may be used to make triple-decker sandwich coordination compounds by reacting a half-sandwich coordination complex as described above with a double-decker sandwich coordination compound (e.g., a heteroleptic or homoleptic double-decker sandwich coordination compound), preferably in a polar aprotic solvent, and preferably at a temperature of at least 100° C., to produce the triple-decker sandwich coordination compound. Preferably at least one of the three porphyrinic macrocycles involved in the reaction (one in the half-sandwich coordination complex; the other two in the double-decker sandwich coordination compound) is different from the others, so that the triple-decker sandwich coordination compounds so made are heteroleptic sandwich coordination compounds. Since these reactions may be carried out in a one-pot fashion, the reaction conditions for this step may be essentially the same or the same as the reaction conditions described above for synthesis of the half-sandwich coordination complexes. The triple decker sandwich coordination compounds may be purified for subsequent use in accordance with known techniques. The reaction may be carried out under essentially the same conditions described above, preferably under dry conditions.

Triple-decker sandwich coordination compounds produced by the methods of the present invention can be used for any purpose, including but not limited to the manufacture of high density memory devices as described in U.S. Pat. No. 6,212,093 to Lindsey.

The present invention is explained in greater detail in the following non-limiting Examples.

EXAMPLES

The (Pc)Eu(Pc)Eu(Por) type of triple decker was employed for attachment via a thiol linker to an electroactive surface. The reasons were two-fold. (1) Only one thiol linker per triple decker was sought in order to avoid the complications that might arise with rotational isomers if two linkers were present. Rotational isomers have been reported in a cerium double decker containing two different porphyrins (Takeuchi, et al. (1998) *Tetrahedron Lett.* 39:7897–7900; Sugasaki, et al. (1999) *J. Chem. Soc., Perkin Trans.* 1:3259–3264). (2) The synthetic chemistry of porphyrins is better developed than that of phthalocyanines (Lindsey, J. S. (2000) In: *The Porphyrin Handbook;* Kadish, K. M., Smith, K. M., Guilard, R., Eds.; Academic Press: San Diego, Calif., Vol. 1, pp 45–118). Thus, a synthetic handle in triple deckers would be more easily introduced via a suitably functionalized porphyrin monomer than with a phthalocyanine. This work led to a set of thiol-derivatized (Pc)Eu(Pc)Eu(Por) triple deckers, which yielded self-assembled monolayers on gold electrodes with electrochemical properties suitable for molecular-based information storage (Li, et al. (2000) *J. Org. Chem.* 65:7379–7390; Gryko, et al. (2001) *J. Mater. Chem.* 11: 1162–1180).

The solution electrochemical properties of the three types of triple deckers with a variety of substituted (but not thiol-derivatized) porphyrin and phthalocyanine rings were examined. The motivation for this work was to identify suitable pairs of triple deckers that exhibit interleaving of oxidation potentials, thereby affording the opportunity for increased density of information storage. In a number of cases, the triple decker of type (Por)Eu(Pc)Eu(Por) constituted one or both members of the pair of triple deckers. Triple deckers of type (Por$^1$)M(Pc)M(Por$^2$) are not available via the "reaction-of-monomers" synthesis. To minimize the arduous chromatography associated with the preparation of triple deckers of type (Pc)Eu(Pc)Eu(Por) which have been worked with extensively, and to gain access to triple deckers of type (Por$^1$)Eu(Pc)Eu(Por$^2$) in which only one porphyrin bears a thiol linker, directed "monomer+dimer" syntheses of triple-decker compounds were investigated.

A directed synthesis of heteroleptic heteronuclear triple deckers has been described by Weiss's group (Chabach, et al. (1996) *Angew. Chem. Int. Ed. Engl.* 35:898–899). The reaction of a (Por$^1$)M$^1$(acac) half-sandwich complex (M$^1$= Gd, Lu and Y) and a double decker (Por$^2$)M$^2$(Pc) (M$^2$=La, Ce) in refluxing 1,2,4-trichlorobenzene afforded triple deckers of the type (Por$^1$)M$^1$(Pc)M$^2$(Por$^2$) in high yields (64–81%) with no other triple deckers reported (supra). This "monomer+dimer" method has rarely been used. In one application, "PcLi$_2$, M(acac)$_3$, and (Pc')M(Pc') (terms defined below) were reacted in refluxing 1,2,4-trichlorobenzene. In all cases examined, a mixture of ("Pc) M(Pc')M(Pc') and ("Pc)M(Pc')M("Pc) was obtained (Liu, et al. (2000) *Inorg. Chim. Acta* 310:140–146). To date, the Weiss method has not been applied with a (Pc)M(Pc) double decker to obtain the (Pc)Eu(Pc)Eu(Por) triple decker.

These studies were begun by applying the Weiss method in pursuit of the (Pc)Eu(Pc)Eu(Por) or (Por$^1$)Eu(Pc)Eu (Por$^2$) complexes. A single triple decker was obtained with this method in some applications but mixtures of triple deckers in other applications. The mixtures of triple deckers likely result from cleavage of the double decker under the high temperature conditions of the synthesis. Such limitations in scope prompted the inventors to investigate rational routes that proceed at lower temperature for the synthesis of heteroleptic triple deckers.

This study describes results obtained upon application of the "monomer+dimer" method of Weiss. It also describes experiments aimed at developing new synthetic methods for the preparation of triple-decker compounds. The method developed here employs a reactive, non-acac lanthanide reagent that is formed in situ; the reaction of this complex with a porphyrin affords the half-sandwich complex. The reaction of the latter with a double decker affords the corresponding triple decker. Several triple deckers of the type (Por$^1$)M$^1$(Pc)M$^2$(Por$^2$) or (Pc)M$^1$(Pc)M$^2$(Por) have been prepared in this manner, where M$^1$ or M$^2$=Eu or Ce. Among the lanthanides, cerium is particularly attractive because cerium triple deckers exhibit metal-centered oxidation states in addition to the four ligand-centered cationic oxidation states (Duchowski and Bocian (1990) *J. Am. Chem. Soc.* 112:8807–8811). The investigation of the information-storage properties of these compounds will be described elsewhere.

Results and Discussion

The porphyrins and phthalocyanines employed in the following studies are shown in Chart 1. For nomenclature, the terms (Por) and (Pc) are used to indicate a generic porphyrin or phthalocyanine entity in a sandwich architecture without regard to the nature of the substituents. For clarity, the unsubstituted free base phthalocyanine is denoted "PcH$_2$. Specific substituted porphyrin or phthalocyanine compounds are denoted with appropriate prefixes to indicate the nature of the substituents.

CHART 1

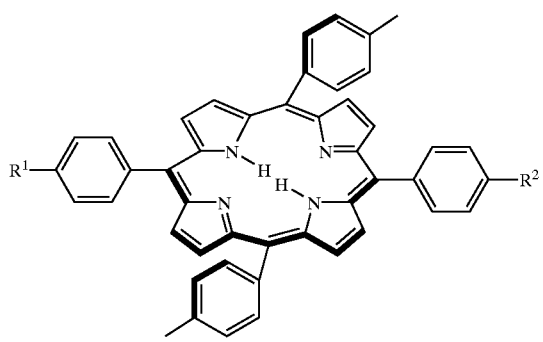

| | |
|---|---|
| R$^1$ = R$^2$ = I | 1-PorH$_2$ |
| R$^1$ = TMS-ethynyl; R$^2$ = TIPS-ethynyl | 2-PorH$_2$ |
| R$^1$ = TMS-ethynyl; R$^2$ = I | 3-PorH$_2$ |

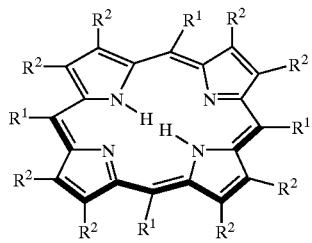

| | |
|---|---|
| R$^1$ = CH$_3$—C$_6$H$_4$/R$^2$ = H | TTPH$_2$ |
| R$^1$ = C$_6$H$_5$/R$^2$ = H | TPPH$_2$ |
| R$^1$ = pentyl/R$^2$ = H | PnPH$_2$ |
| R$^1$ = H/R$^2$ = C$_2$H$_5$ | OEPH$_2$ |

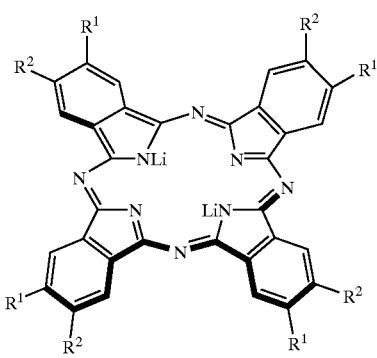

| | |
|---|---|
| R$^1$ = R$^2$ = H | "PcLi$_2$ |
| R$^1$ = R$^2$ = octyloxy | (octyloxy)$_8$PcLi$_2$ |
| R$^1$/R$^2$ = H; (CH$_3$)$_3$C | tBPcLi$_2$ |
| R$^1$ = R$^2$ = heptyl | (heptyl)$_8$PcLi$_2$ |

CHART 1-continued

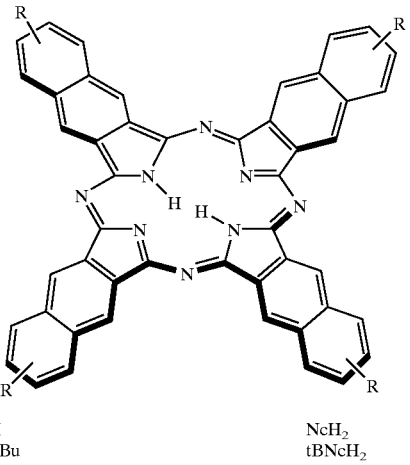

| | |
|---|---|
| R = H | NcH$_2$ |
| R = t-Bu | tBNcH$_2$ |

I. Synthesis of Triple Deckers using Eu(acac)$_3$.nH$_2$O.

The Weiss method for preparing triple deckers of the type (Por$^1$)M$^1$(Pc)M$^2$(Por$^2$) proceeded as follows (Chabach, et al. (1996) *Angew. Chem. Int. Ed. Engl.* 35:898–899). A porphyrin was treated with excess M$^1$(acac)$_3$.nH$_{20}$ in refluxing 1,2,4-trichlorobenzene for 4 h, affording the (Por$^1$)M$^1$(acac) complex. This complex was treated with the mixed double-decker species (Por$^2$)M$^2$(Pc) and refluxing was continued for 8 h. The efforts to prepare triple deckers of type (Pc)Eu(Pc)Eu(Por) or (Por$^1$)Eu(Pc)Eu(Por$^2$) in a rational manner by applying the Weiss method are described below.

Reaction of (Por)Eu(acac) with (Pc)Eu(Pc).

Treatment of TTPH$_2$ with excess Eu(acac)$_3$.nH$_2$O in refluxing 1,2,4-trichlorobenzene afforded the corresponding (TTP)Eu(acac) half-sandwich complex. Treatment of the latter with the unsubstituted ("Pc)$_2$Eu double decker (vide infra) gave the expected triple decker (TTP)Eu("Pc)Eu("Pc) in 24% yield accompanied by unreacted starting materials (Scheme 1). The low yield may stem in part from the low solubility of the double-decker and triple-decker complexes, which caused difficulties in the chromatographic separation process. Nonetheless, these results show that the Weiss method could be applied with the bis(phthalocyanine) double decker ("Pc)$_2$Eu to obtain the expected triple decker (TTP)Eu("Pc)Eu("Pc) in a rational manner.

Scheme 1

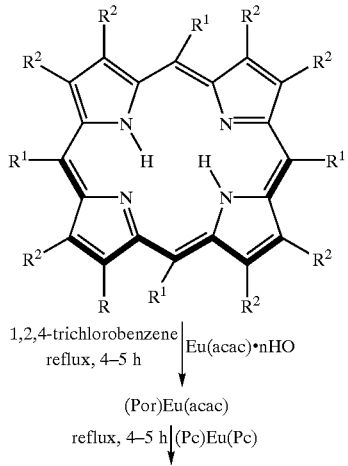

-continued

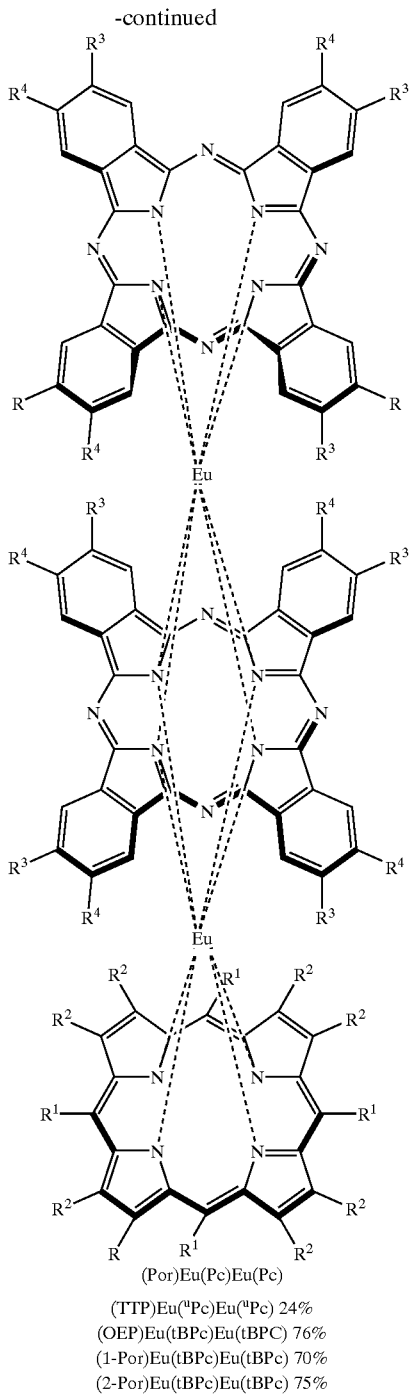

(TTP)Eu("Pc)Eu("Pc) 24%
(OEP)Eu(tBPc)Eu(tBPC) 76%
(1-Por)Eu(tBPc)Eu(tBPc) 70%
(2-Por)Eu(tBPc)Eu(tBPc) 75%

The use of tetra-tert-butylphthalocyanine (consisting of a mixture of regioisomers) for the preparation of triple deckers was found to improve the solubility of the sandwich complexes. The reaction of 5,15-bis(4-iodophenyl)-10,20-di-p-tolylporphyrin (1-PorH$_2$) with Eu(acac)$_3$.nH$_2$O followed by the double decker (tBPc)$_2$Eu (vide infra) in 1,2,4-trichlorobenzene gave the triple decker (1-Por)Eu(tBPc)Eu (tBPc) in 70% yield. Similarly, the reaction of 5-[4-[2-(trimethylsilyl)ethynyl]phenyl]-15-[4-[2-(triisopropylsilyl) ethynyl]phenyl]-10,20-di-p-tolylporphyrin (2-PorH$_2$) or octaethylporphyrin (OEPH$_2$) gave the triple decker (2-Por) Eu(tBPc)Eu(tBPc) in 75% yield or the triple decker (OEP) Eu(tBPc)Eu(tBPc) in 76% yield, respectively (Scheme 1). In each case, no other triple decker was observed. Thus, higher yields were obtained with the more soluble double decker (tBPc)$_2$Eu than with ("PC)$_2$Eu in the reaction with (Por)Eu (acac) in refluxing 1,2,4-trichlorobenzene. The triple deckers with iodo or ethyne substituents are valuable building blocks. The reaction of (TTP)Eu(acac) with the phthalocyanine double decker [(heptyl)$_8$Pc]$_2$Eu (vide infra) proved to be unsuccessful. This result may stem from steric congestion of the alkyl groups on the periphery of the phthalocyanine in the expected triple decker. Indeed, the reaction of (heptyl)$_8$ PcLi$_2$ and octaethylporphyrin under the standard "reaction-of-monomers" conditions afforded exclusively the triple decker of type [(heptyl)$_8$Pc]Eu(Por)Eu[(heptyl)$_8$Pc] (Gryko, et al. (2001) *J. Mater. Chem.* 11:1162–1180).

Each triple-decker complex was characterized by LD-MS, FAB-MS, UV-Vis spectroscopy and $^1$H NMR spectroscopy. However, $^1$H NMR spectroscopy was not particularly useful for the characterization of complexes containing the tetra-tert-butylphthalocyanine ligand due to the presence of phthalocyanine regioisomers (Sommerauer, et al. (1996) *J. Am. Chem. Soc.* 118:10085–10093). The purity of the complexes was confirmed by TLC and LD-MS analysis.

Reaction of (TPP)Eu(acac) with (TTP)Eu("Pc).

Treatment of TPPH$_2$ with excess Eu(acac)$_3$.nH$_2$O in refluxing 1,2,4-trichlorobenzene afforded the corresponding (TPP)Eu(acac) half-sandwich complex. Treatment of the latter with the mixed double decker (TTP)Eu("Pc) (vide infra) and further refluxing afforded a mixture of the three possible triple deckers of type (Por)Eu("Pc)Eu(Por); in other words a mixture of (Por$^1$)Eu("Pc)Eu(Por$^1$), (Por$^1$)Eu("Pc) Eu(Por$^2$), and (Por$^2$)Eu("Pc)Eu(Por$^2$) as shown in Scheme 2. The presence of the components in the mixture was observed by LD-MS and $^1$H NMR spectroscopy. Such a mixture results from cleavage of the starting double decker prior to the formation of the triple-decker complexes. Traces of the triple deckers (Por$^1$)Eu("Pc)Eu("Pc) and (Por$^2$)Eu ("Pc)Eu("Pc) were also found in the mixture which further reflects cleavage of the double decker. The separation of the mixtures of triple deckers of the same type was not possible, due to the similarities of the substituents in the porphyrins TTPH$_2$ and TPPH$_2$.

Scheme 2

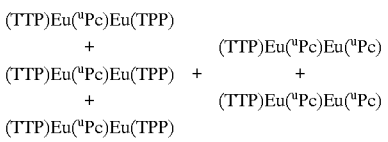

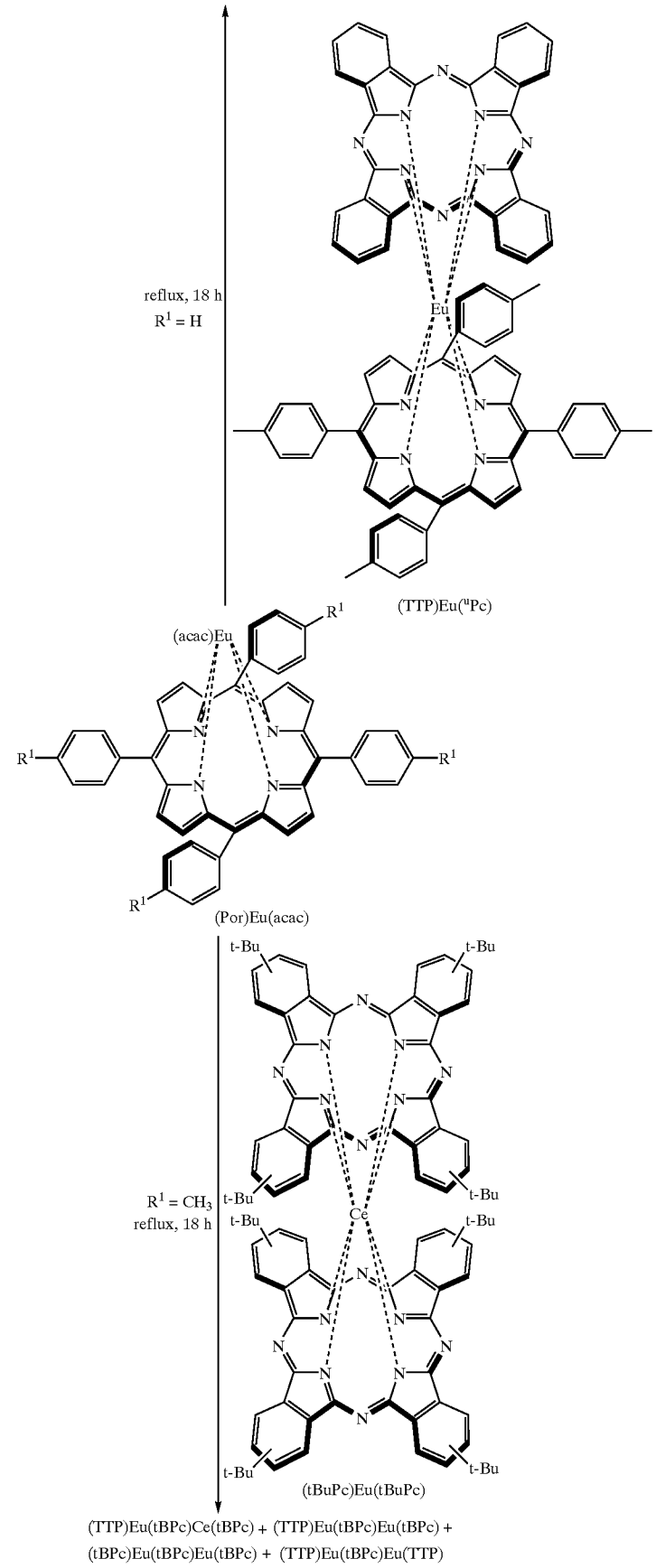
(TTP)Eu(tBPc)Ce(tBPc) + (TTP)Eu(tBPc)Eu(tBPc) +
(tBPc)Eu(tBPc)Eu(tBPc) + (TTP)Eu(tBPc)Eu(TTP)

Reaction of (TTP)Eu(acac) with (tBPc)Ce(tBPc).

Treatment of TTPH$_2$ with excess Eu(acac)$_3$.nH$_2$O in refluxing 1,2,4-trichlorobenzene afforded the corresponding (TTP)Eu(acac) half-sandwich complex. Treatment of the latter with the double decker (tBPc)Ce(tBPc) (vide infra) and further refluxing afforded a mixture of several triple deckers of type (tBPc)Ce(tBPc)Eu(TTP) (main product in the crude mixture), (tBPc)Eu(tBPc)Eu(TTP), (tBPc)Eu(tBPc)Eu(tBPc) and (TTP)Eu(tBPc)Eu(TTP) as shown in Scheme 2. The presence of the components in the mixture was observed by LD-MS. Chromatographic separation of the expected (tBPc)Ce(tBPc)Eu(TTP) triple decker and the undesired (tBPc)Eu(tBPc)Eu(TTP) was not possible. Such a mixture results from cleavage of the starting double decker prior to the formation of the triple-decker complexes. Double deckers are known to undergo cleavage. Indeed, Buchler's "raise-by-one-story" synthesis employs reaction of (Por)M(Por) alone to give the triple decker (Por)M(Por)M(Por) (Buchler, et al. (1988) *Inorg. Chem.* 27:339–345). Phthalocyanine-containing double deckers also undergo cleavage, as shown by the mixture of products obtained upon application of the Weiss "monomer+dimer" synthesis method by Liu et al. ((2000) *Inorg. Chim. Acta* 310:140–146). A control experiment was performed to confirm that such scrambling results from the cleavage of the starting double decker and not from rearrangement of a triple-decker product. A sample of (TTP)Eu("Pc)Eu("Pc) (Li, et al. (2000) *J. Org. Chem.* 65:7379–7390) was heated under the conditions of the Weiss method [excess Eu(acac)$_3$ in refluxing 1,2,4-trichlorobenzene] for 22 h. No scrambling was observed; however, the slow decomposition of the triple decker yielding TTPH$_2$ and ("Pc)Eu("Pc) was observed.

II. Investigation of Replacements for Eu(acac)$_3$.nH$_2$O.

To find milder reaction conditions that could be used in the preparation of triple deckers, thereby avoiding the scrambling observed in some applications of the Weiss method, lanthanide precursors in place of Eu(acac)$_3$.nH$_2$O that could be reacted at lower temperatures were sought. The first experiments focused on the europium salts EuCl$_3$, EuI$_2$, Eu(OTf)$_3$, Eu(acac)$_3$.nH$_2$O and Eu(2,2,6,6-tetramethyl-3,5-heptanedionate)$_3$. These salts were used in metalation reactions with the porphyrins TTPH$_2$ or TPPH$_2$ in various solvents (DMF, THF, DME, bis(2-methoxyethyl) ether) as well as with different bases (DBU, 2,6-lutidine) under reflux conditions. The state of metalation of the porphyrin was readily characterized by UV-Vis spectroscopy. In some cases partial metalation of the porphyrin occurred but the subsequent reaction with "PcLi$_2$ for preparing the desired sandwich complex did not give a clean product distribution.

To obtain the clean formation of a europium porphyrin half-sandwich complex that was stable in solution, we tried to substitute the ligands on the europium center by organic substituents through reaction of EuX$_3$ (X=Cl, OTf, acac or 2,2,6,6-tetramethyl-3,5-heptanedionate) with RLi [R=tert-butyl, butyl, Si(SiMe$_3$)$_3$, N(SiMe$_3$)$_2$] in bis(2-methoxyethyl) ether. The only known compounds related to these experiments are EuCl[N(SiMe$_3$)$_2$]$_2$ (Aspinall, et al. (1989) *J. Chem. Soc., Dalton Trans.* 623–626) and Eu[N(SiMe$_3$)$_2$]$_3$ (Bradley, et al. (1973) *J. Chem. Soc., Dalton Trans.* 1021–1023). The latter complex was used for metalation of porphyrins by Wong et al.((1999) *J. Chem. Soc., Dalton Trans.* 3053–3062). Of the various RLi reagents examined, facile metalation yielding a europium porphyrin half-sandwich complex was obtained by using the amide ligand (R=N(SiMe$_3$)$_2$) in reaction with EuCl$_3$. The process, which is quite similar to the reported procedure (Aspinall, et al. (1989) *J. Chem. Soc., Dalton Trans.* 623–626), employed the following steps: (1) to a vigorously stirred suspension of EuCl$_3$ in bis(2-methoxyethyl) ether at 0° C. was slowly added two molar equiv of LiN(SiMe$_3$)$_2$ in THF, (2) warming to room temperature (1 h) and then stirring for 1 h, (3) addition of the porphyrin, and (4) refluxing the mixture for 3 h. In this manner, a stable solution of the porphyrin half-sandwich complex (Por)EuCl was obtained as evidenced by UV-Vis spectroscopy. Use of 3 molar equiv of LiN(SiMe$_3$)$_2$, which affords Eu[N(SiMe$_3$)$_2$]$_3$, as performed by Aspinall, et al. ((1989) *J. Chem. Soc., Dalton Trans.* 623–626) did not afford stable solutions of the europium porphyrin half-sandwich. The (Por)EuCl half-sandwich complex is expected to react with a dilithium phthalocyanine to give sandwich complexes. The bifunctional europium complex EuCl[N(SiMe$_3$)$_2$]$_2$ provides distinct avenues of reaction with a free base versus a dilithium porphyrinic macrocycle. The reaction with a free base porphyrin in the formation of a half-sandwich complex would lead to amine elimination (—HN(SiMe$_3$)$_2$). The subsequent reaction with a dilithium phthalocyanine should give elimination of salt (—LiCl). This type of bifunctional reactivity cannot occur with a reagent such as MX$_3$. Note that the structure envisaged for the (Por)EuX half sandwich has X=Cl. The alternative structure where X=N(SiMe$_3$)$_2$ appears much less likely, given that the porphyrin half-sandwich complex derived from Eu[N(SiMe$_3$)$_2$]$_3$ was not stable and underwent slow demetalation. This method was developed for the more demanding case of preparing the europium porphyrin half-sandwich complex, but applied later to both porphyrins and phthalocyanines. However, the reaction with a free base phthalocyanine affords the bis(phthalocyanine) double decker rather than the half-sandwich complex.

III. Synthesis of Double Deckers and Triple Deckers using EuCl[N(SiMe$_3$)$_2$]$_2$.

The synthesis of triple deckers was the main focus of this work. However, to probe the reactivity of the (Por)EuCl half-sandwich complex, we first investigated the synthesis of double deckers using this reagent.

(Por)Eu(Pc) Double Deckers.

The porphyrin was added to a 4-fold excess of EuCl[N(SiMe$_3$)$_2$]$_2$ prepared in situ in bis(2-methoxyethyl) ether and the resulting mixture was refluxed for ca. 3 h. Bis(2-methoxyethyl) ether has bp 162° C.; the oil bath temperature for these reactions was set at ~170° C. The metalation of the porphyrin leads to a change in the pattern of the Q-bands in the absorption spectrum, as reported by Wong et al. ((1983) *Inorg. Synth.* 22:156–162). The metalated porphyrin was stable in dilute solution as determined by UV-Vis spectroscopy; in contrast, the metalated porphyrin product obtained from Eu[N(SiMe$_3$)$_2$]$_3$ (also prepared in situ) demetalated in dilute solution over the course of a few minutes. The expected structure of the metalated product derived from EuCl[N(SiMe$_3$)$_2$]$_2$ is shown in Scheme 3. Note that additional solvent and/or salt molecules may be coordinated to the europium center. (An X-ray study on crystals grown from a toluene solution of metalated meso-tetra-p-tolylporphyrin failed because of lack of reflexes.)

Scheme 3

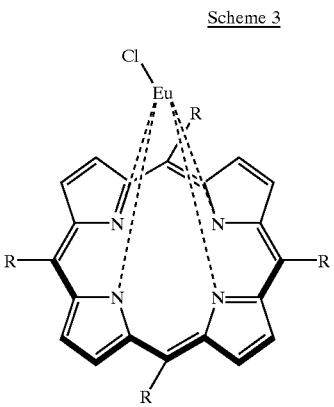

The europium porphyrin half-sandwich complex was then treated with a dilithium phthalocyanine to obtain sandwich complexes. The best results were obtained by using a two-fold excess of a dilithium phthalocyanine, because the latter reacts with the porphyrin half-sandwich as well as with the excess $EuCl[N(SiMe_3)_2]_2$ remaining from the porphyrin metalation process. The main products in these reactions were the double-decker complexes (Por)Eu(Pc) and (Pc)Eu (Pc) (Scheme 4). The separation was performed by repeated column chromatography, typically two silica columns ($CHCl_3$) followed by an SEC column (THF). During the course of the first column chromatography procedure, the reduced (Por)Eu(Pc)⁻ (green) and $(Pc)_2Eu^-$ (blue) double-decker species were oxidized to the corresponding neutral forms [brown for (Por)Eu(Pc); green for $(Pc)_2Eu$]. This type of behavior has been described by Jiang et al. ((1988) *Polyhedron* 17:3903–3908). To overcome the low solubility of the ⁿPc-containing complexes, prior to the chromatographic work up, the crude reaction mixture was stirred overnight with silica gel in $CHCl_3$ to oxidize the reduced species of the double deckers, yielding the neutral forms.

Scheme 4

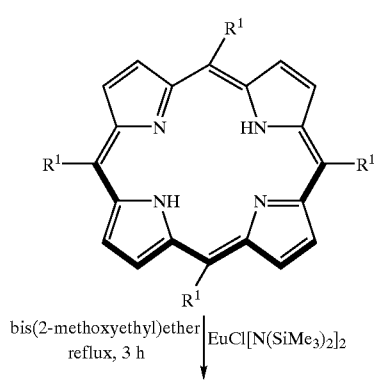

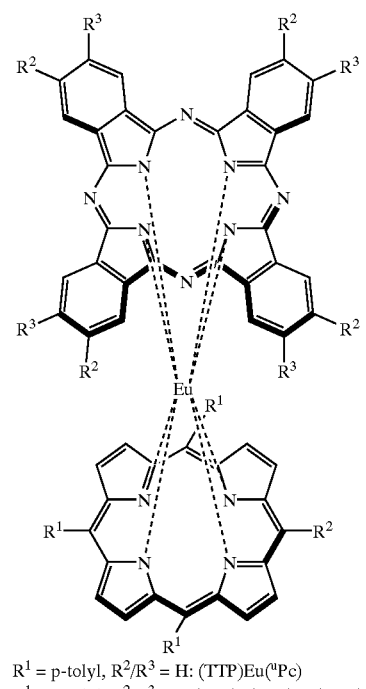

$R^1$ = p-tolyl, $R^2/R^3$ = H: (TTP)Eu(ⁿPc)
$R^1$ = p-tolyl, $R^2/R^3$ = H/(t-Bu): (TTP)Eu(tBPc)

+

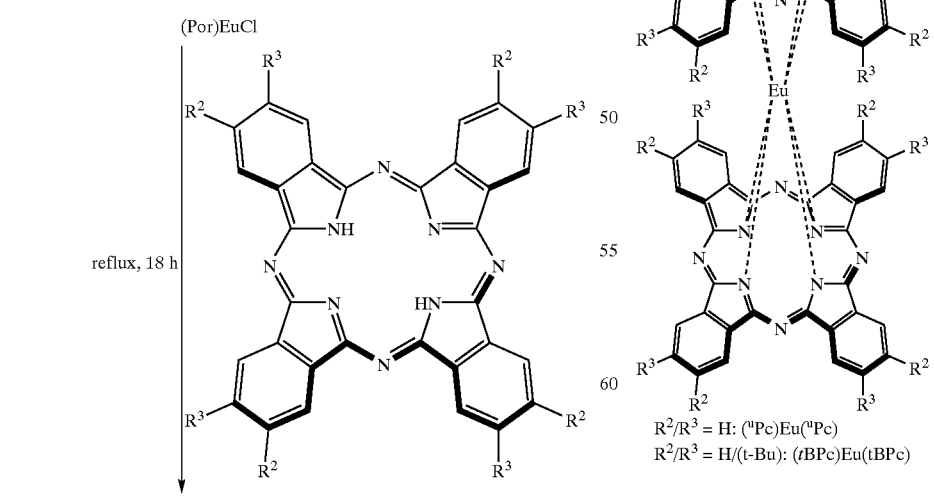

$R^2/R^3$ = H: (ⁿPc)Eu(ⁿPc)
$R^2/R^3$ = H/(t-Bu): (tBPc)Eu(tBPc)

Thus, treatment of the EuCl[N(SiMe$_3$)$_2$]$_2$ solution with TTPH$_2$ gave the metalated porphyrin. The subsequent reaction with unsubstituted phthalocyanine "PcH$_2$ afforded the (TTP)EU("Pc) double decker in 38% yield. The use of dilithium tetra-tert-butylphthalocyanine in the same reaction gave the double decker (TTP)Eu(tBPc) in 94% yield (Scheme 4).

(Pc)Eu(Pc) Double Deckers.

For the preparation of phthalocyanine sandwich complexes, studies of the reaction of a free base phthalocyanine with the EuCl[N(SiMe$_3$)$_2$]$_2$ reagent prepared in situ were performed. In general, the reaction of a solution of EuCl[N(SiMe$_3$)$_2$]$_2$ and a free base phthalocyanine in refluxing bis(2-methoxyethyl) ether for 5–18 h gave the corresponding (Pc)Eu(Pc) double decker. Thus, the reaction of "PcH$_2$, tBPcH$_2$, tBNcH$_2$, (heptyl)$_8$PcH$_2$, or (octyloxy)$_8$PcH$_2$ gave ("Pc)$_2$Eu, (tBPc)$_2$Eu, (tBNc)$_2$Eu, [(heptyl)$_8$Pc]$_2$Eu, or [(octyloxy)$_8$Pc]$_2$Eu in yields >61% (Scheme 5). A trial to make the double decker of 1,4,8,11,15,18,22,25-octabutoxyphthalocyanine failed and led to the decomposition of the starting material. These results show the higher reactivity of the phthalocyanines compared to the porphyrins. The only byproducts observed in these reactions were the free base phthalocyanine starting material, and in the case of the tetra-t-butylphthalocyanine, traces of the homoleptic triple decker (tBPc)Eu(tBPc)Eu(tBPc) as observed by preparative SEC and analysis by LD-MS. Separation was achieved by one silica column (CHCl$_3$) and one SEC (THF) column [except for the reaction with "PcH$_2$, due to solubility problems]. The low solubility of complexes containing the unsubstituted phthalocyanine caused problems in the separation process. In this case, prior to the chromatographic work up, the crude reaction mixture was stirred overnight with silica gel in CHCl$_3$ to oxidize the reduced species of the double decker, yielding the neutral form. In so doing, better separation in the chromatographic step (silica, CHCl$_3$) was obtained.

Scheme 5

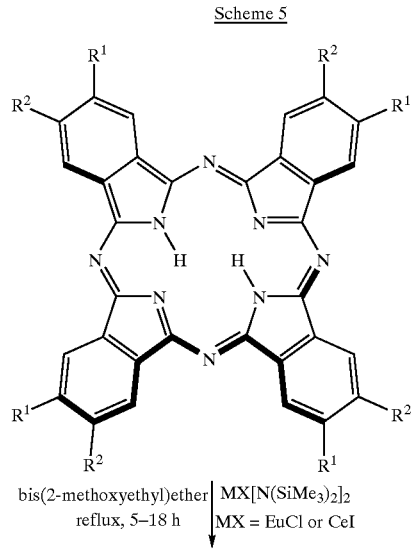

bis(2-methoxyethyl)ether  MX[N(SiMe$_3$)$_2$]$_2$
reflux, 5–18 h  MX = EuCl or CeI

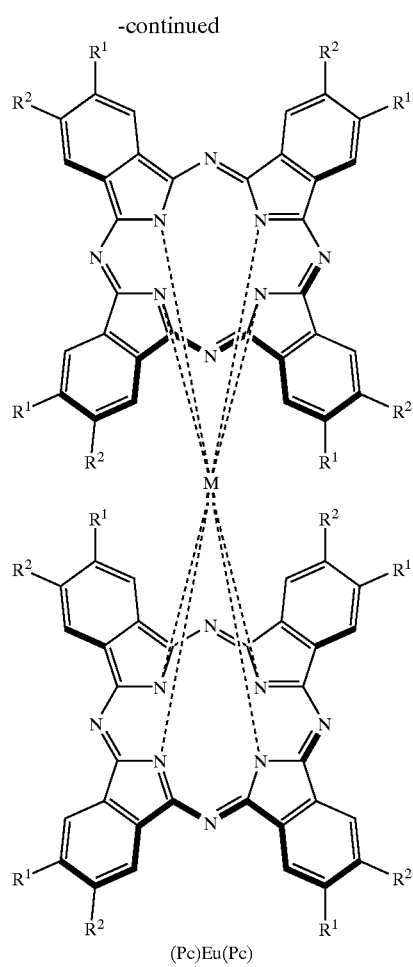

(Pc)Eu(Pc)

M = Eu
R$^1$ = R$^2$ = H: 71%
R$^1$/R$^2$ = H/(t-Bu): 78%
R$^1$ = R$^2$ = heptyl: 83%
R$^1$ = R$^2$ = octyloxy: 90%

M = Ce
R$^1$/R$^2$ = H/(t-Bu): 74%
R$^1$ = R$^2$ = octyloxy: 66%

It is noteworthy that a variety of methods have been developed for the synthesis of lanthanide double deckers, including directed routes and statistical routes Homoleptic phthalocyanine double deckers have been prepared by cyclotetramerization of a phthalonitrile in the presence of a Ln(OAc)$_3$ alone (Kirin, et al. (1965) *Russ. J. Inorg Chem.* 10:1065–1066) or under Shiraishi conditions (Tomoda, et al. (1980) *Chem. Lett.* 1277–1280; Tomoda, et al. (1983) *Chem. Lett.* 313–316) in the presence of DBU in a long-chain alcohol at reflux (Jiang, et al. (1997) *Polyhedron* 16:515–520; Jiang, et al. (2000) *Eur. J. Inorg Chem.* 205–209; De Cian, et al. (1985) *Inorg. Chem.* 24:3162–3167; Nyokong, et al. (2000) *Inorg. Chem.* 39:128–135). Homoleptic porphyrin double deckers have been prepared by reaction of a free base porphyrin with Ln(acac)$_3$ in refluxing 1,2,4-trichlorobenzene (Buchler, et al. (1983) *Z. Naturforsch.* 38b:1339–1345) or by reaction of a (porphyrin)M(acac) half-sandwich complex with a porphyrin-dilithium species (Buchler and Scharbert (1988) *J. Am. Chem. Soc.* 110:4272–4276). Heteroleptic porphyrin double deckers have been prepared via a statistical reaction of two free base porphyrins with a Ln(acac)$_3$ in refluxing 1,2,4-trichlorobenzene (Buchler, et al. (1989) *Chem. Ber.* 2219–2228). Heteroleptic phthalocyanine double deckers have been prepared via statistical reaction of two dilithium phthalocyanines in the presence of a Ln(acac)$_3$ in refluxing chloronaphthalene (Pondaven, et al. (1992) *New J. Chem.* 16:711–718; Pondaven, et al. (1991) *New J. Chem.* 15:515–516; Cadiou, et al. (1999) *J. Org. Chem.* 64:9046–9050). A directed approach employed reaction of a PcLi$_2$ with a Ln(acac)$_3$ to form the (Pc)M(acac) half-sandwich complex, which provides a template to direct the cyclotetramerization of a phthalonitrile under Shiraishi conditions (Tomoda, et al. (1980) *Chem. Lett.* 1277–1280; Tomoda, et al. (1983) *Chem. Lett.* 313–316) to form the second phthalocyanine (Jiang, et al. (1998) *Inorg. Chim. Acta* 268:141–144). Porphyrin-phthalocyanine double deckers have been prepared via a number of routes: (a) directed reaction of a PcLi$_2$ with a Ln(acac)$_3$ at 120° C. to form the half-sandwich complex, followed by reaction with a free base porphyrin in refluxing 1,2,4-trichlorobenzene (Tran-Thi, et al. (1994) *J. Phys. Chem.* 98:8279–8288); (b) directed reaction of a (Pc)M(acac) with a free base porphyrin, or a (Por)M(acac) with a PcLi$_2$, in refluxing 1,2,4-trichlorobenzene (Chabach, et al. (1995) *J. Am. Chem. Soc.* 117:8548–8556); (c) directed reaction under Shiraishi conditions (Tomoda, et al. (1980) *Chem. Lett.* 1277–1280; Tomoda, et al. (1983) *Chem. Lett.* 313–316) using a (Por)M(acac) as a template to direct the cyclotetramerization of a phthalonitrile (Jiang, et al. (1988) *Polyhedron* 17:3903–3908; Jiang, et al. (1999) *Chem. Lett.* 261–262); (d) a one-flask reaction under Shiraishi conditions (Tomoda, et al. (1980) *Chem. Lett.* 1277–1280; Tomoda, et al. (1983) *Chem. Lett.* 313–316) of a free base porphyrin, Ln(acac)$_3$, and a naphthalonitrile (Jiang, et al. (2001) *Eur. J. Inorg. Chem.* 413–417). The route described herein is a directed route. In some respects, the directed route described herein resembles Linstead's method in the original discovery of double deckers, in which (Pc)SnCl$_2$ was reacted with PcLi$_2$ affording the corresponding (Pc)Sn(Pc) (Barrett, et al. (1936) *J. Chem. Soc.* 1719–1736). A directed route is superior to statistical procedures for the preparation of heteroleptic porphyrin double deckers or heteroleptic phthalocyanine double deckers. A directed route is not needed to prepare homoleptic phthalocyanine double deckers or homoleptic porphyrin double deckers.

Triple Deckers.

To prepare triple deckers, the porphyrin half-sandwich (Por)EuCl was reacted with several different double-decker compounds. The double deckers were used in the neutral or reduced forms. The reduced form of the (Por)Eu(Pc) double decker (Por=TTP; Pc="Pc or tBPc) was generated in bis(2-methoxyethyl) ether by reaction with an equimolar amount of NaBH$_4$ in bis(2-methoxyethyl) ether at room temperature for 24 h. In the course of this reaction the mixture underwent a characteristic change in color from brown to green. The reduced form of the (Pc)$_2$Eu double decker (Pc="Pc or tBPc) was obtained by reaction of the neutral double decker with one molar equivalent of NaBH$_4$, affording a color change from green to blue during the course of reduction. All double-decker species containing the unsubstituted phthalocyanine were poorly soluble in the bis(2-methoxyethyl) ether. Triple-decker complexes were only obtained by using double-decker complexes containing the tetra-tert-butylphthalocyanine (tBPc) in reactions with the europium porphyrin half-sandwich complex.

The triple decker (TTP)Eu(tBPc)Eu(tBPc) was obtained in two different reactions starting with (TTP)EuCl. The reaction of (TTP)EuCl (3 or 1.5 molar equiv) with either the neutral or reduced form of the double decker (tBPc)$_2$Eu in refluxing bis(2-methoxyethyl) ether for 20 h afforded the triple decker in 16% or 17% yield, respectively. The reaction of (Por)EuCl and a double-decker species was performed for 20 h at reflux in bis(2-methoxyethyl) ether. The product was isolated by chromatography (one silica column, one SEC column). Yields are based on the amount of the bis (phthalocyanine) species. Compared with the good yields obtained in the reactions of the (Por)Eu(acac) half-sandwich complex with the (tBPc)$_2$Eu double decker (vide supra) in refluxing 1,2,4-trichlorobenzene via the Weiss method, these approaches using a (Por)EuCl half-sandwich complex showed that triple deckers of type (Por)Eu(tBPc)Eu(tBPc) could be obtained under these conditions but afforded no improvement in yield.

Triple deckers of the type (Por$^1$)M(tBPc)M(Por$^2$) are highly desirable for information-storage applications but have not yet been employed in these applications due to lack of suitable synthetic methods. We investigated the synthesis of these types of triple deckers by the reaction of the (TPP)EuCl half-sandwich complex with the double-decker species (Por)Eu(Pc) (Por=TTP; Pc="Pc or tBPc). The reaction using the double decker (TTP)Eu("Pc) met with failure. After reaction of (TPP)EuCl with (TTP)Eu(tBPc) for 24 h in refluxing bis(2-methoxyethyl) ether, the LD-MS spectrum of the reaction mixture showed a peak indicating that the expected triple decker (TPP)Eu(tBPc)Eu(TTP) was a minor product. However, the isolated yield was quite low and insufficient material was obtained for full characterization. A longer reaction time afforded no increase in yield. The reduced form of the double decker afforded a similar reaction pattern.

In summary, the reaction of the (Por)EuCl half-sandwich complex with a suitable phthalocyanine double decker affords the corresponding triple decker. The reaction is performed at lower temperature (~170° C.) than the Weiss method (~230° C.), affords the triple decker devoid of scrambling albeit in low yield, and works with the tBPc but not the "Pc ligand. While the restriction to the use of the tBPc ligand may seem quite limiting, triple deckers composed of ligands bearing electron-releasing substituents are highly attractive for information storage applications (Gryko, et al. (2001) *J. Mater. Chem.* 11: 1162–1180). In addition, the presence of the t-butyl substituents affords increased solubility. Thus the scope of this method was examined using the tBPc macrocycle. To examine the effects of lanthanide salts with better leaving groups than chloride, CeI$_3$ was used as a starting material. LuI$_3$ was also tried under the same conditions employed with CeI$_3$. However, no metalation of the porphyrin was observed by UV-Vis spectroscopy. Cerium-containing triple deckers are attractive for molecular information storage applications given their additional cationic oxidation states compared with those of other lanthanide triple deckers.

IV. Synthesis of Double Deckers and Triple Deckers using CeI[N(SiMe$_3$)$_2$]$_2$.

The procedure for the in situ preparation of EuCl[N (SiMe$_3$)$_2$]$_2$ was applied to CeI$_3$ with minor changes. (1) The CeI$_3$ was treated with 2 molar equiv of LiN(SiMe$_3$)$_2$ (THF solution) in bis(2-methoxyethyl) ether at 0° C. (2) The solution was allowed to warm to room temperature (1 h) and after that the mixture was refluxed for 1 h to obtain complete reaction of the CeI$_3$ (CeI$_3$ in the form of beads reacts to completion only under vigorous conditions). The resulting solution of CeI[N(SiMe$_3$)$_2$]$_2$ was used in reactions with porphyrins [ratio of Ce:porphyrin >4:1] to obtain the corresponding (Por)CeI half-sandwich complexes. The completeness of metalation was again estimated by UV-Vis spectroscopy. It is noteworthy that the (Por)CeI complexes formed stable solutions, similar to the case of the (Por)EuCl half sandwich complex. In contrast, (Por)Ce(acac) complexes have been reported to be unstable (Wong, C. -P. (1983) Inorg. Synth. 22:156–162). In the following, we examine the synthesis of double deckers as a prelude to the synthesis of triple deckers.

(Por)Ce(tBPc) Double Deckers.

The reaction of TTPH$_2$ with the CeI[N(SiMe$_3$)$_2$]$_2$ reagent (generated in solution) followed by treatment with an equimolar amount of tBPcLi$_2$ gave the green double decker (TTP)Ce(tBPc) in 72% yield. The use of PnPH$_2$ in the same reaction led to (PnP)Ce(tBPc) in 57% yield (Scheme 6). Thus, the reaction of the (Por)CeI half-sandwich complex with an equimolar amount of tBPcLi$_2$ cleanly gave the double-decker species (Por)Ce(tBPc). In contrast to the reaction with the europium analogue, in these reactions no bis(phthalocyanine) double decker (i.e., (tBPc)$_2$Ce) was observed. The different color (green) of (Por)Ce(Pc) complexes compared with that of the europium double deckers (Por)Eu(Pc) (brown) is attributed to the different redox states of the metals and ligands: the europium complex is formulated as (Por$^{2-}$)Eu$^{3+}$(Pc$^{3\cdot}$ .); the cerium complex as (Por$^{2-}$)Ce$^{4+}$(Pc$^{2-}$).

Scheme 6

CeI[N(SiMe$_3$)$_2$]$_2$ bis(2-methoxyethyl)ether
reflux, 3 h | PorH$_2$

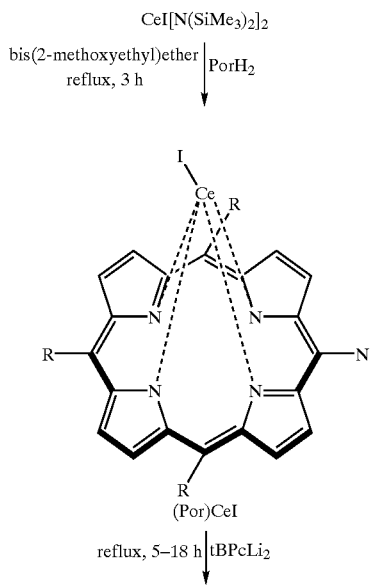

(Por)CeI reflux, 5–18 h | tBPcLi$_2$

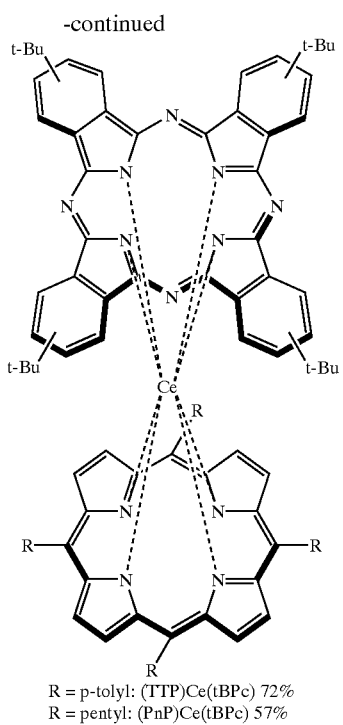

R = p-tolyl: (TTP)Ce(tBPc) 72%
R = pentyl: (PnP)Ce(tBPc) 57%

(Pc)Ce(Pc) Double Deckers.

The reaction of tBPcH$_2$ with the CeI[N(SiMe$_3$)$_2$]$_2$ reagent (generated in solution) gave the green double decker (tBPc)Ce(tBPc) in 74% yield. The use of (octyloxy)$_8$PcH$_2$ in the same reaction led to [(octyloxy)$_8$Pc]Ce[(octyloxy)$_8$Pc] in 66% yield (Scheme 5). Thus, the reaction of the PcH$_2$ with an excess of CeI[N(SiMe$_3$)$_2$]$_2$ complex cleanly gave the double-decker species (Pc)Ce(Pc). A trial to make the double decker of 1,4,8,11,15,18,22,25-octabutoxyphthalocyanine failed and led to the decomposition of the starting material.

Triple Deckers.

The absence of the (tBPc)Ce(tBPc) double decker in the reactions to make the heteroleptic double deckers suggested that tBPcLi$_2$ exhibits preference for reaction with the cerium porphyrin half-sandwich complex versus the CeI[N(SiMe$_3$)$_2$]$_2$. Thus, we examined reactions of the (Por)CeI half-sandwich complex with only 0.5 equiv of tBPcLi$_2$ (relative to the porphyrin). Considering the greater reactivity of this half-sandwich complex and no side reaction of tBPcLi$_2$ with the excess CeI[N(SiMe$_3$)$_2$]$_2$, the triple decker of type (Por)Ce(tBPc)Ce(Por) should be produced. This expectation was confirmed by using meso-tetra-p-tolylporphyrin or meso-tetrapentylporphyrin in reactions with CeI[N(SiMe$_3$)$_2$]$_2$ followed by treatment with 0.5 equiv of tBPcLi$_2$; the triple decker (TTP)Ce(tBPc)Ce(TTP) or (PnP)Ce(tBPc)Ce(PnP) was obtained in 14% or 13% yield, respectively. The double-decker complex (TTP)Ce(tBPc) or (PnP)Ce(tBPc) was isolated as a byproduct in 43% or 40% yield, respectively (Scheme 7). However, an attempt to prepare the (TTP)Ce(Nc)Ce(TTP) triple decker by this method met with recovery of the starting materials, probably because of the poor solubility of the NcLi$_2$ in the reaction mixture.

Scheme 7

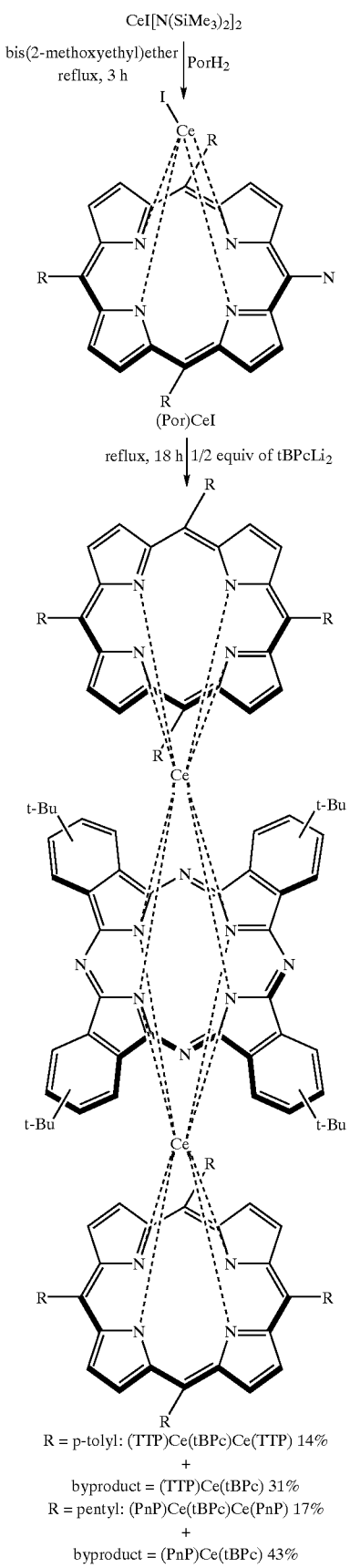

R = p-tolyl: (TTP)Ce(tBPc)Ce(TTP) 14%
+
byproduct = (TTP)Ce(tBPc) 31%
R = pentyl: (PnP)Ce(tBPc)Ce(PnP) 17%
+
byproduct = (PnP)Ce(tBPc) 43%

The success in preparing triple deckers of the type (Por)Ce(tBPc)Ce(Por) prompted us to explore the use of the (Por)CeI half-sandwich complex in a building block approach. The reaction of the (Por)EuCl half-sandwich complex with the neutral or reduced form of (tBPc)$_2$Eu gave the (Por)Eu(tBPc)Eu(tBPc) triple decker in nearly identical yield. In further studies we used the neutral form of each double-decker complex, which is the species normally obtained upon purification.

Our first studies focused on the use of (Por)Ce(Pc) double deckers. The reaction of the (PnP)CeI half-sandwich complex with (TTP)Ce(tBPc) gave a mixture comprised predominantly of three triple deckers of type (Por)Ce(tBPc)Ce(Por) in almost statistical ratio (estimated by LD-MS). This intractable mixture of (Por$^1$)Ce(tBPc)Ce(Por$^1$), (Por$^1$)Ce(tBPc)Ce(Por$^2$), and (Por$^2$)Ce(tBPc)Ce(Por$^2$) likely stems from cleavage of the double decker prior to the formation of the triple decker. Further evidence concerning scrambling in these types of reactions was obtained in the reactions of the (TTP)CeI half-sandwich with the bis(phthalocyaninato) double deckers (tBPc)Ce(tBPc) and [(octyloxy)$_8$Pc]2Ce. These reactions mostly afforded the (TTP)Ce(Pc) type double deckers along with the starting double decker and a tiny amount of the expected triple decker. These results also suggest cleavage of the starting double decker.

Given that both the heteroleptic and the homoleptic double deckers of cerium are unstable under these reaction conditions, by using a europium double decker in the reaction with the (Por)CeI half sandwich we hoped to avoid such scrambling processes. Thus, the reaction of (TTP)CeI with the double decker (tBPc)$_2$Eu or [(octyloxy)$_8$Pc]$_2$Eu in refluxing bis(2-methoxyethyl) ether for 18 to 24 h gave the expected triple decker (TTP)Ce(tBPc)Eu(tBPc) or (TTP)Ce[(octyloxy)$_8$Pc]Eu[(octyloxy)$_8$Pc] in 55% or 39% yield. In the case of the [(octyloxy)$_8$Pc]$_2$Eu double-decker reaction, TTPH$_2$ was used in excess because use of a stoichiometric ratio of the starting materials resulted in difficulty of separating the triple decker and starting double decker. Accordingly, the yield has been calculated from the amount of double decker used. Similarly, the reaction of (OEP)CeI with the (tBPc)$_2$Eu double decker in refluxing bis(2-methoxyethyl)ether for 18 h gave the expected triple decker (OEP)Ce(tBPc)Eu(tBPc) in 38% yield (Scheme 8).

Scheme 8

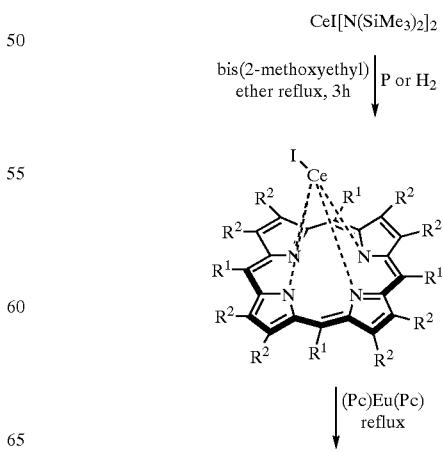

Scheme 8

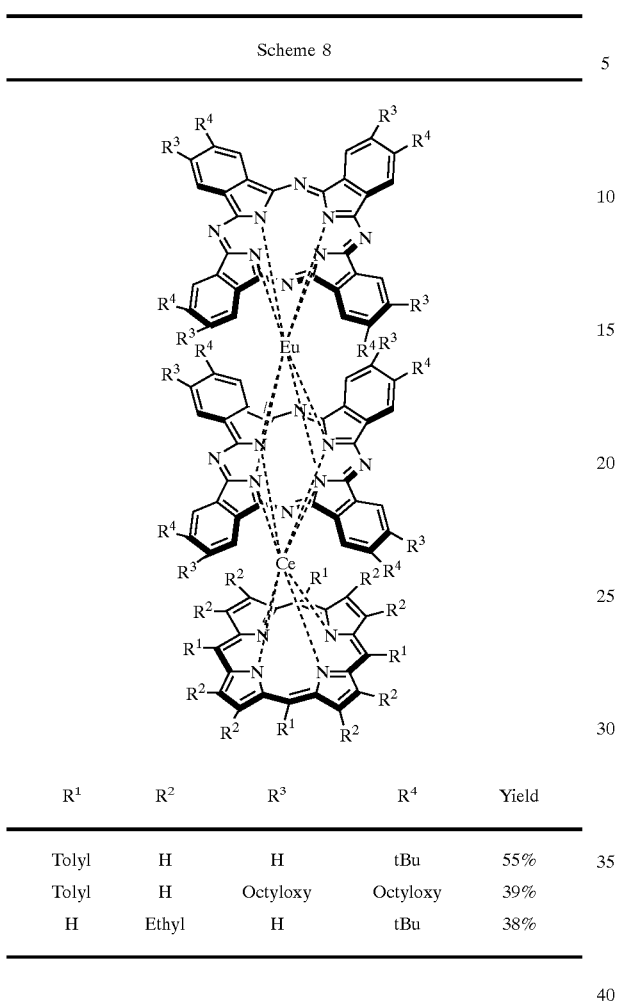

| R[1] | R[2] | R[3] | R[4] | Yield |
|------|------|------|------|-------|
| Tolyl | H | H | tBu | 55% |
| Tolyl | H | Octyloxy | Octyloxy | 39% |
| H | Ethyl | H | tBu | 38% |

The synthesis of triple deckers of type (Por[1])Eu(tBPc)Ce(Por[2]) was examined. The reaction of (PnP)CeI and (TTP)Eu(tBPc) for 3 h in refluxing bis(2-methoxyethyl)ether gave the expected triple decker (PnP)Ce(tBPc)Eu(TTP) in 57% yield (Scheme 9). No other triple deckers were obtained. This approach was applied to the synthesis of a triple decker bearing two functional handles. Thus, the reaction of CeI[N(SiMe$_3$)$_2$]$_2$ with a mono-iodo mono-ethynyl porphyrin (3-PorH$_2$) (Rao, et al. (2000) *J. Org. Chem.* 65:7323–7344) afforded the corresponding cerium porphyrin half-sandwich complex. Reaction of the latter with (TTP)Eu(tBPc) in refluxing bis(2-methoxyethyl) ether for 18 h afforded the triple decker (3-Por)Ce(tBPc)Eu(TTP) in 36% yield (Scheme 10). Traces of other triple deckers were observed by LD-MS; these species were removed by SEC. This particular triple decker (3-Por)Ce(tBPc)Eu(TTP) is an ideal building block for elaboration into arrays.

Scheme 9

CeI[N(SiMe$_3$)$_2$]$_2$ bis(2-methoxyethyl)ether, reflux, 3 h | PnPH$_2$

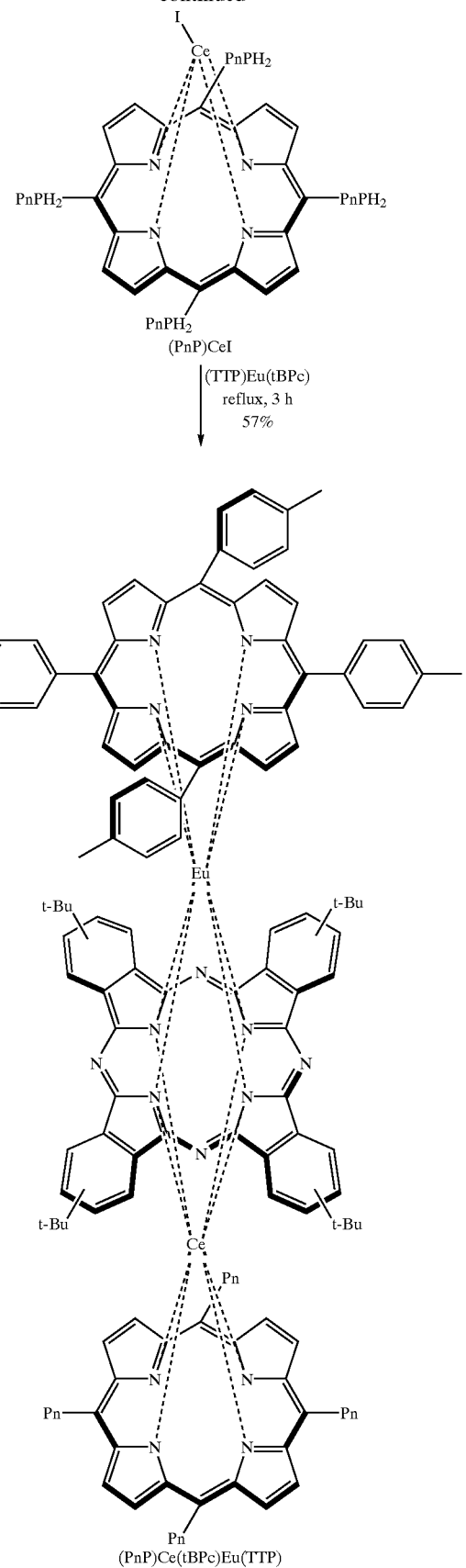

(PnP)Ce(tBPc)Eu(TTP)

Scheme 10

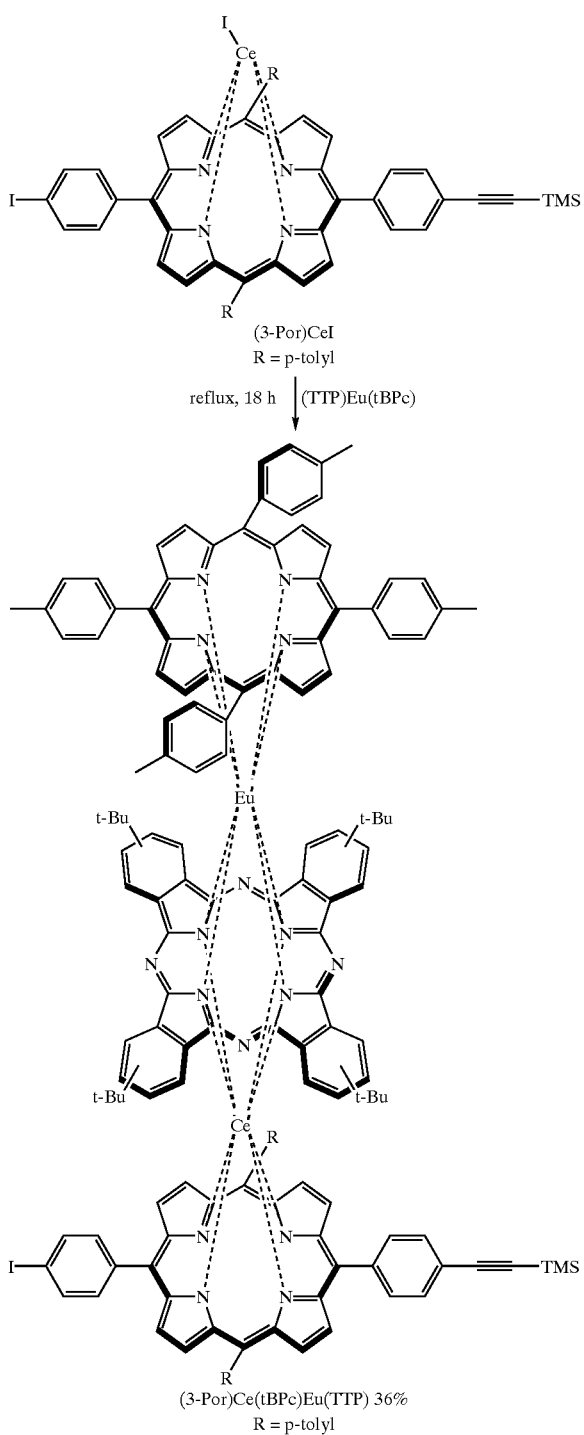

(3-Por)CeI
R = p-tolyl reflux, 18 h | (TTP)Eu(tBPc)

(3-Por)Ce(tBPc)Eu(TTP) 36%
R = p-tolyl

In summary, the reaction of the (Por)CeI half-sandwich complex and either a (tBPc)$_2$Eu double decker or a (Por)Eu(tBPc) double decker afforded the expected triple decker in good yield, generally with little or no observable scrambling. This approach affords facile access to triple deckers of the type (tBPc)Eu(tBPc)Ce(Por) or (Por$^1$)Eu(tBPc)Ce(Por$^2$).

Conclusions.

The use of lanthanide porphyrin-phthalocyanine triple-decker sandwich molecules for molecular information storage applications requires synthetic methodology that enables (1) the selective preparation of a given type of triple decker, (2) the incorporation of substituents at desired locations on the ligands in the triple deckers, and (3) incorporation of two lanthanides of choice in the triple decker. The common "reaction-of-monomers" synthesis of lanthanide triple deckers affords a mixture of double deckers and triple deckers comprised of one metal, and does not enable the introduction of different substituents in the two porphyrin or two phthalocyanine ligands in the triple decker. This method constrained our initial studies in molecular information storage to the use of triple deckers of type (Pc)Eu(Pc)Eu(Por). The directed "monomers+dimers" synthesis of Weiss (demonstrated with M Gd, Lu, Y, La and Ce) employs the reaction of a (Por$^1$)M$^1$(acac) half-sandwich complex with a (Pc)M$^2$(Por$^2$) double-decker complex in refluxing 1,2,4-trichlorobenzene (bp 214° C.). Greater selectivity is obtained as the main product is the (Por$^1$)M$^1$(Pc)M$^2$(Por$^2$) in the cases reported. We applied this method as described herein to obtain several (Pc)Eu(Pc)Eu(Por) triple deckers with good results. However, application of this method to prepare the (Por$^1$)Eu(Pc)Eu(Por$^2$) triple decker gave a mixture of triple deckers.

We have developed a somewhat milder method that employs a lanthanide reagent MX[N(SiME$_3$)$_2$]$_2$ (MX=EuCl or CeI), generated in situ, which is reacted with a porphyrin in refluxing bis(2-methoxyethyl) ether (bp 162° C.) to give the porphyrin half-sandwich complex (Por)MX. With MX=EuCl, the subsequent reaction with a dilithium phthalocyanine gave the double-decker complexes (Por)Eu(Pc) and (Pc)Eu(Pc). The reaction of (Por)EuCl with (tBPc)Eu(tBPc) gave the corresponding triple decker (tBPc)Eu(tBPc)Eu(Por). With MX=CeI, subsequent reaction with one molar equiv of tBPcLi$_2$ gave the (Por)Ce(tBPc) double decker; the subsequent reaction with 0.5 molar equiv of tBPcLi$_2$ gave the (Por)Ce(tBPc)Ce(Por) triple decker accompanied by the (Por)Ce(tBPc) double decker. The (Por$^1$)CeI half-sandwich complex was used in reactions with europium double deckers [e.g., (Por$^2$)Eu(tBPc), (tBPc)$_2$Eu] to prepare the triple deckers (Por$^1$)Ce(tBPc)Eu(Por$^2$) and (Por$^1$)Ce(tBPc)Eu(tBPc). The rational synthesis of heteroleptic heteronuclear triple-decker complexes by reaction of a porphyrinic half-sandwich complex with a double-decker compound allows the specific introduction of a functionalized porphyrin into the triple decker for further incorporation into triple-decker arrays. The ability to prepare (Por$^1$)Ce(tBPc)Eu(Por$^2$) is especially attractive, because one porphyrin can be derivatized with synthetic handles (e.g., thiol linkers or groups for preparing arrays) while the second porphyrin carries substituents selected to alter the electrochemical potential of the complex. The application of this method to prepare triple-decker monomers for incorporation into arrays for multibit information storage is presently under investigation.

Experimental Section

General.

$^1$H NMR spectra were collected in CDCl$_3$ (300 MHz) unless noted otherwise. Absorption spectra (HP 8451A, Cary 3) were collected in toluene. Porphyrin-phthalocyanine sandwich complexes were analyzed by laser desorption mass spectrometry (LD-MS; Bruker Proflex II) and high resolution fast atom bombardment mass spectrometer (FAB-MS; JEOL HX 110HF). LD-MS analysis was done without a matrix (Fenyo, et al. (1997) *J. Porphyrins Phthalocyanines* 1:93–99; Srinivasan, et al. (1999) *J. Porphyrins Phthalocyanines* 3:283–291) or with the matrix 1,2-bis(5-phenyloxazol-2-yl)benzene (POPOP). High resolution mass spectrometry was carried out at greater than unit resolution.

¹H NMR spectroscopy proved uninformative for all double deckers as well as for those triple deckers comprised of tetra-t-butyl substituted phthalocyanine regioisomers. The double deckers were generally characterized by TLC, UV-Vis, LD-MS, and FAB-MS. The triple deckers were characterized by TLC, UV-Vis, ¹H NMR, LD-MS, and FAB-MS.

All operations involving organometallic compounds were carried out under argon using standard Schlenk techniques. Eu(acac)$_3$·nH$_2$O was obtained from Alfa Aesar. Bis(2-methoxyethyl) ether was used as received from Aldrich (anhydrous, water <0.005%). Unless otherwise indicated, all other reagents were obtained from Aldrich Chemical Company, and all solvents were obtained from Fisher Scientific. The following phthalocyanines were obtained commercially: tetra-tert-butylphthalocyanine (tBPcH$_2$, mixture of regioisomers), naphthalocyanine (NcH$_2$), tetra-tert-butylnaphthalocyanine (tBNcH$_2$, mixture of regioisomers), 2,3,9,10,16,17,23,24-octakis(octyloxy)phthalocyanine [(octyloxy)$_8$PcH$_2$] and dilithium phthalocyanine ("PcLi$_2$, dye content 70%) were obtained from Aldrich; phthalocyanine ("PcH$_2$) was obtained from Kodak; octaethylporphyrin (OEPH$_2$) was obtained from Midcentury Chemicals. 2,3,9,10,16,17,23,24-Octaheptylphthalocyanine (Nishi, et al. (1992) *Heterocyclic Chem.* 29:475) [(heptyl)$_8$PcH$_2$] was obtained as a by-product of statistical reactions yielding mixtures of phthalocyanines (Yang, et al. (2000) *J. Mater. Chem.* 10:283–296). The dilithium derivative tBPcLi$_2$ was prepared from 4-tert-butylphthalonitrile (Pondaven, et al. (1992) *New J. Chem.* 16:711–718; Hanack, et al. (1982) *Chem. Ber.* 115:2836–2853); the other dilithium phthalocyanines [(octyloxy)$_8$PcLi$_2$, (heptyl)$_8$PcLi$_2$, NcLi$_2$] were prepared by lithiation of the free base following the literature procedure. Synthetic porphyrins were prepared via the Adler method (Adler, et al. (1967) *J. Org. Chem.* 32:476) (meso-tetra-p-tolylporphyrin, meso-tetraphenylporphyrin), the two-step one-flask synthesis (meso-tetrapentylporphyrin) (Lindsey, et al. (1987) *J. Org. Chem.* 52:827–836), or via new rational synthetic methods [5,15-bis(4-iodophenyl)-10,20-di-p-tolylporphyrin (1-PorH$_2$) (Schweikart, et al. manuscript in preparation), 5-[4-[2-(trimethylsilyl)ethynyl]phenyl]-15-[4-[4-[2-(triisopropylsilyl)ethynyl]phenyl]-10,20-di-p-tolylporphyrin (2-PorH$_2$) (Schweikart, et al. manuscript in preparation), 5-(4-iodophenyl)-15-[4-[2-(trimethylsilyl)ethynyl]phenyl]-10,20-di-p-tolylporphyrin (3-PorH$_2$) (Rao, et al. (2000) *J. Org. Chem.* 65:7323–7344)].

Calculated yields for porphyrin-containing sandwich molecules are based on the amount of porphyrin employed. The yields for (Pc)Eu(Pc) double deckers are based on the phthalocyanine. The number of moles of a PcLi$_2$ compound is taken to be 70% for a given mass of "PcLi$_2$ and 100% for tBPcLi$_2$. For Eu(acac)$_3$·nH$_2$O, the value of n is assumed to be 2.5 for calculating the quantity of material in the reactions.

Chromatography.

Adsorption column chromatography was performed using flash silica (Baker, 60–200 mesh). Preparative-scale size exclusion chromatography (SEC) was performed using Bio-Rad Bio-beads SX-1. A preparative-scale glass column (4.8×60 cm) was packed using Bio-beads SX-1 in THF and eluted with gravity flow (Wagner, et al. (1996) *J. Am. Chem. Soc.* 118:11166–11180). Analytical scale SEC was performed with a Hewlett-Packard 1090 HPLC using a 1000 Å column (5 μL, styrene-divinylbenzene copolymer) with THF as eluent (0.8 mL/min) (supra).

1. Europium Double Deckers: Exemplary Procedure for the in situ Preparation of EuCl[N(SiMe$_3$)$_2$]$_2$, Given for the Synthesis of (TTP)Eu("Pc).

To a vigorously stirred suspension of EuCl$_3$ (100.7 mg, 0.390 mmol) in bis(2-methoxyethyl) ether (5 mL) at 0° C. was slowly added a solution of LiN(SiMe$_3$)$_2$ (780 μL, 0.780 mmol, 1M in THF). Stirring was continued while the mixture was allowed to warm to room temperature (ca. 1 h). The mixture was stirred at room temperature for 1 h. (This constitutes the standard procedure for preparing EuCl[N(SiMe$_3$)$_2$]$_2$ in situ.) A sample of meso-tetra-p-tolylporphyrin (45.3 mg, 67.6 μmol) was added. The mixture was refluxed in an oil bath at 170° C. for ca. 3 h while the progress of the reaction was monitored by UV-Vis spectroscopy. After metalation of the porphyrin was complete, "PcLi$_2$ (102 mg, 135 μmol) was added and the mixture was further refluxed for 18 h. The mixture was cooled, concentrated and CHCl$_3$ (100 mL) and silica gel (15 g) were added. This mixture was stirred overnight which led to a color change from green to brown-green. The mixture was concentrated and chromatographed (silica, CHCl$_3$), affording three bands (first band purple, second band brown, third band green). The first band was not collected. The third band was again chromatographed and finally washed with hexanes to give ("Pc)Eu ("Pc) (Jiang, et al. (1997) *Polyhedron* 16:515–520) as a green solid (49 mg, 62%). The second band was further chromatographed (silica, toluene) to give the title compound as a brown solid (34.0 mg, 38%). LD-MS obsd 1333.39; FAB-MS obsd 1333.7, calcd 1333.37 (C$_{80}$H$_{52}$N$_{12}$Eu); $\lambda_{abs}$ 324, 407, 476 nm.

(TTP)Eu(tBPc).

The reaction of EuCl[N(SiMe$_3$)$_2$]$_2$, produced from EuCl$_3$ (60.2 mg, 0.233 mmol) and LiN(SiMe$_3$)$_2$ (466 μL, 0.466 mmol, 1M in THF) in bis(2-methoxyethyl)ether (5 mL) following the standard procedure, and meso-tetra-p-tolylporphyrin (39.0 mg, 58.2 μmol) gave after 3 h of reflux the solution of metalated porphyrin, as determined by UV-Vis. A sample of tBPcLi$_2$ (84.5 mg, 0.115 mmol) was added and the mixture refluxed overnight (18 h). The mixture was cooled and concentrated. The residue was chromatographed (silica, CHCl$_3$), during which slow oxidation of the reduced form of the double deckers took place. Separation was obtained by repeating the same column to give two bands (first band brown, second band green). The first band (brown) was further purified by two SEC columns (THF) to give the title compound as a brown solid (85.4 mg, 95%). LD-MS obsd 1557.6, 1542.51; FAB-MS obsd 1557.62, calcd 1557.62 (C$_{96}$H$_{84}$N$_{12}$Eu); $\lambda_{abs}$ 330, 408, 476 nm. The second band (green) gave after SEC (THF) the green double decker (tBPc)Eu(tBPc) (9.6 mg, 10%).

("Pc)EU("Pc).

EuCl[N(SiMe$_3$)$_2$]$_2$ was produced in situ from EuCl$_3$ (111.9 mg, 0.433 mmol) and LiN(SiMe$_3$)$_2$ (866 μL, 0.866 mmol, 1M in THF) in bis(2-methoxyethyl) ether (5 mL) following the standard procedure. A sample of "PcH$_2$ (42.4 mg, 82.5 μmol) was added and the mixture refluxed for 6 h. The mixture was cooled, concentrated and CHCl$_3$ (100 mL) and silica gel (15 g) were added. This mixture was stirred overnight which led to a color change from blue to green. The mixture was concentrated and chromatographed (silica, CHCl$_3$). The only band (green) was collected, affording a green solid (34.2 mg, 71%). Analytical data were consistent with the literature (Jiang, et al. (1997) *Polyhedron* 16:515–520).

(tBPc)Eu(tBPc).

EuCl[N(SiMe$_3$)$_2$]$_2$ was produced in situ from EuCl$_3$ (48.2 mg, 0.186 mmol) and LiN(SiMe$_3$)$_2$ (373 μL, 0.373 mmol, 1M in THF) in bis(2-methoxyethyl) ether (3 mL) following the standard procedure. A sample of tBPcH$_2$ (38.3 mg, 51.9 μmol) was added and the mixture refluxed for 4 h. The mixture was cooled, concentrated and chromatographed (silica, CHCl$_3$). The first band (light blue, tBPcH$_2$) was not collected. The second band (green) was further purified by SEC (THF), affording a green solid (32.4 mg, 78%). Analytical data were consistent with the literature (Battisti, et al. (1992) *Chem. Mater.* 4:1323–1328).

(tBNc)Eu(tBNc).

EuCl[N(SiMe$_3$)$_2$]$_2$ was produced in situ from EuCl$_3$ (106.5 mg, 0.412 mmol) and LiN(SiMe$_3$)$_2$ (825 μL, 0.825 mmol, 1M in THF) in bis(2-methoxyethyl) ether (6 mL) following the standard procedure. A sample of tBNcH$_2$ (103.4 mg, 107 μmol) was added and the mixture refluxed for 4 h. The mixture was cooled, concentrated and chromatographed (silica, CHCl$_3$/methanol). The only band (blue) was collected, affording a blue solid (65.7 mg, 61%). Analytical data were consistent with the literature (Jiang, et al. (2000) *Eur. J. Inorg. Chem.* 205–209).

[(Octyloxy)$_8$Pc]$_2$Eu.

EuCl[N(SiMe$_3$)$_2$]$_2$ was produced in situ from EuCl$_3$ (78.5 mg, 0.303 mmol) and LiN(SiMe$_3$)$_2$ (606 μL, 0.606 mmol, 1M in THF) in bis(2-methoxyethyl) ether (5 mL) following the standard procedure. A sample of (octyloxy)$_8$PcH$_2$ (76.9 mg, 49.9 μmol) was added and the mixture refluxed for 6 h. The mixture was cooled, concentrated and chromatographed (silica, CHCl$_3$). The first band (green) was collected and further purified by SEC (THF), affording a green solid (71.7 mg, 90%). Analytical data were consistent with the literature (Liu, et al. (2000) *Aust. J. Chem.* 53:131–135).

[(Heptyl)$_8$Pc]$_2$Eu.

EuCl[N(SiMe$_3$)$_2$]$_2$ was produced in situ from EuCl$_3$ (70.0 mg, 0.271 mmol) and LiN(SiMe$_3$)$_2$ (542 μL, 0.542 mmol, 1M in THF) in bis(2-methoxyethyl) ether (5 mL) following the standard procedure. A sample of (heptyl)$_8$PcH$_2$ (86.5 mg, 66.7 μmol) was added and the mixture refluxed for 4 h. The mixture was cooled, concentrated and chromatographed (silica, CHCl$_3$). The first band (green) was collected and further purified by SEC (THF), affording a green solid (76.2 mg, 83%). Analytical data were consistent with the literature (Jiang, et al. (1997) *Polyhedron* 16:515–520).

2. Synthesis of Triple Decker of Type (Por)Eu(Pc)Eu(Pc) via the Weiss Procedure; Given for (TTP)Eu("Pc)Eu("Pc).

A mixture of meso-tetra-p-tolylporphyrin (12.5 mg, 18.6 μmol) and Eu(acac)$_3$.nH$_2$O (32 mg, 0.065 mmol) in 1,2,4-trichlorobenzene (8 mL) was heated to reflux in an oil bath at ~230° C. and stirred for 4 h. The resulting cherry-red solution (containing the (TTP)Eu(acac) half-sandwich complex) was cooled to room temperature, and then the double decker ("Pc)Eu("Pc) (22 mg, 0.019 mmol) was added. The mixture was refluxed for 18 h. Then the solvent was removed and the residue was chromatographed (silica, CHCl$_3$). The first band (purple, TTPH$_2$) was not collected. The second band (green) was collected and redissolved in CHCl$_3$/toluene for chromatography on silica (toluene). The first band afforded a green solid (8.8 mg, 24%). Analytical data were consistent with the literature (Li, et al. (2000) *J. Org. Chem.* 65:7379–7390).

(OEP)Eu(tBPc)Eu(tBPc).

A mixture of octaethylporphyrin (OEPH$_2$) (9.6 mg, 0.018 mmol) and Eu(acac)$_3$.nH$_2$O (62.3 mg, 0.126 mmol) in 1,2,4-trichlorobenzene (5 mL) was heated to reflux and stirred for 3.5 h. The resulting cherry-red solution was cooled to room temperature, the bis(phthalocyanine) europium double decker (tBPc)Eu(tBPc) (29.3 mg, 0.018 mmol) was added, and the mixture was refluxed for 18 h. The solvent was removed and the residue was chromatographed (silica, CHCl$_3$). The first band (purple, OEPH$_2$) was not collected. The second band [green, (tBPc)Eu(tBPc)] was not collected. The third band (blue) was collected and further purified by SEC (THF). The first band (blue) was collected, affording a blue solid (31.6 mg, 76%). A $^1$H NMR spectrum was collected but the mixture of regioisomers made interpretation difficult. LD-MS (with POPOP) obsd 2310.1, 1626.1, 673.0; FAB-MS obsd 2310.69, 2311.0 calcd (C$_{132}$H$_{140}$N$_{20}$Eu$_2$); λ$_{abs}$ 342, 394, 623, 658, 724 nm.

(1-Por)Eu(tBPc)Eu(tBPc).

A mixture of 1-PorH$_2$ (40 mg, 0.044 mmol) and Eu(acac)$_3$.nH$_2$O (140 mg, 0.284 mmol) in 1,2,4-trichlorobenzene (5 mL) was heated to reflux and stirred for 5 h. The resulting cherry-red solution was cooled to room temperature, the bis(phthalocyanine) europium double decker (tBPc)Eu(tBPc) (72 mg, 0.044 mmol) was added, and the mixture was refluxed for 5 h. The solvent was removed and the residue was chromatographed (silica, CHCl$_3$). The first band (purple, 1-PorH$_2$) was not collected. The second band (green) was collected and further purified twice by SEC (THF). The first band (green-blue) was collected, affording a green-blue solid (82 mg, 70%). A $^1$H NMR spectrum was collected but the mixture of regioisomers made interpretation difficult. LD-MS (with POPOP) obsd 2671.3, 2544.5, 1625.3; FAB-MS obsd 2670.75, calcd 2670.69 (C$_{142}$H$_{126}$N$_{20}$Eu$_2$); λ$_{abs}$ 347, 418, 526, 621, 727 nm.

(2-Por)Eu(tBPc)Eu(tBPc).

A mixture of 2-PorH$_2$ (18 mg, 0.019 mmol) and Eu(acac)$_3$.nH$_2$O (37 mg, 0.075 mmol) in 1,2,4-trichlorobenzene (4 mL) was heated to reflux and stirred for 4 h. The resulting cherry-red solution was cooled to room temperature, the (tBPc)Eu(tBPc) double decker (28 mg, 0.017 mmol) was added, and the mixture was refluxed for 4 h. The solvent was removed and the residue was chromatographed (silica, CHCl$_3$). The first band (purple, 2-PorH$_2$) was not collected. The second band (green) was collected and further purified by SEC (THF). The first band (green-blue) was collected, affording a green-blue solid (38.5 mg, 75%). A $^1$H NMR spectrum was collected but the mixture of regioisomers made interpretation difficult. LD-MS obsd 2693.3, 2678.2; FAB-MS obsd 2695.10, calcd 2695.08 (C$_{158}$H$_{156}$N$_{20}$Eu$_2$); λ$_{abs}$ 347, 418, 527, 621, 729 nm.

3. Cerium Sandwich Complexes: Exemplary Procedure for the in situ Preparation of CeI[N(SiMe$_3$)$_2$]$_2$, Given for the Synthesis of (TTP)Ce(tBPc).

To a vigorously stirred suspension of CeI$_3$ (114 mg, 0.219 mmol) in bis(2-methoxyethyl) ether (5 mL) at 0° C. was slowly added a solution of LiN(SiMe$_3$)$_2$ (439 μL, 0.439 mmol, 1M in THF). Stirring was continued while the mixture was allowed to warm to room temperature (ca. 1 h). The solution was then refluxed in an oil bath at ~170° C. for 1 h, during which the cerium beads reacted and a fine precipitate (presumably LiI) was obtained. This constitutes the standard procedure for preparing CeI[N(SiMe$_3$)$_2$]$_2$ in situ. Then meso-tetra-p-tolylporphyrin (35.1 mg, 52.4 mmol) was added and the mixture was refluxed for ca. 3 h while the progress of the reaction was monitored by UV-Vis spectroscopy. After formation of the porphyrin half-sandwich complex was complete, tBPcLi$_2$ (42.5 mg, 56.7 μmol) was added and the mixture was further refluxed for 5 h. The mixture was cooled and concentrated. The residue was chromatographed [silica, CHCl$_3$, then CHCl$_3$/methanol (10:1)]. No separation was observed, perhaps due to slow decomposition of iodine-complexes of the sandwich molecules. Therefore only one fraction was collected, which was further separated by SEC (THF). The first band (green) was chromatographed again by SEC. A final chromatography (silica, CHCl$_3$) afforded a green solid (57.9 mg, 72%). LD-MS obsd 1544.4, 1530.8, 807.54; FAB-MS obsd 1544.60, calcd 1544.60 (C$_{96}$H$_{84}$N$_{12}$Ce); $\lambda_{abs}$ 338, 403, 470, 628 nm.

(PnP)Ce(tBPc).

A solution of CeI[N(SiMe$_3$)$_2$]$_2$, prepared in situ by reaction of CeI$_3$ (229 mg, 0.441 mmol) and LiN(SiMe$_3$)$_2$ (882 μL, 0.882 mmol, 1M in THF) in bis(2-methoxyethyl) ether (8 mL) following the standard procedure, was reacted with meso-tetrapentylporphyrin (57.3 mg, 97.1 μmol) at reflux for 3 h, affording the metalated porphyrin as determined by UV-Vis. A sample of tBPcLi$_2$ (75.2 mg, 0.100 mmol) was added and the mixture was refluxed for 18 h. The mixture was cooled and concentrated. Chromatography [silica, CHCl$_3$ then CHCl$_3$/methanol (10:1)] gave one band (green) which was further purified by SEC (THF). Final purification on silica (CHCl$_3$) afforded a green solid (80.9 mg, 57%). LD-MS obsd 1463.3, 1407.3, 1394.3; FAB-MS obsd 1466.74, calcd 1466.74 (C$_{88}$H$_{100}$N$_{12}$Ce); $\lambda_{abs}$ 336, 402, 469, 586, 629 nm.

(tBPc)Ce(tBPc).

A solution of CeI[N(SiMe$_3$)$_2$]$_2$, prepared in situ by reaction of CeI$_3$ (139.2 mg, 0.267 mmol) and LiN(SiMe$_3$)$_2$ (535 μL, 0.535 mmol, 1M in THF) in bis(2-methoxyethyl) ether (5 mL) following the standard procedure, was reacted with tBPcH$_2$ (51.1 mg, 67.1 μmol) at reflux for 20 h. The mixture was cooled, concentrated, and chromatographed [silica, CHCl$_3$ then CHCl$_3$/methanol (10:1)]. The first band (blue, tBPcH$_2$) was not collected. The second band (green) was further purified by SEC (THF). The first band (green) was collected, affording a green solid (40.2 mg, 74%). Analytical data were consistent with the literature (Tomilova, et al. (1984) *Zh. Obshch. Khim.* 54:1678–1679).

[(Octyloxy)$_8$Pc]$_2$Ce.

A solution of CeI[N(SiMe$_3$)$_2$]$_2$, prepared by in situ reaction of CeI$_3$ (194.1 mg, 0.373 mmol) and LiN(SiMe$_3$)$_2$ (746 μL, 0.746 mmol, 1M in THF) in bis(2-methoxyethyl) ether (6 mL) following the standard procedure, was reacted with (octyloxy)$_8$PcH$_2$ (142.8 mg, 92.7 μmol) at reflux for 17 h. The mixture was cooled, concentrated, and chromatographed (silica, CHCl$_3$). The second band (green) was collected and further purified by SEC (THF). The second band (green) was collected, affording a green solid (98.8 mg, 66%). $^1$H NMR δ 0.96 (t, J=7.5 Hz, 48H), 1.3–1.7 (m, 128H), 1.7–1.9 (m, 32H), 2.2 (dt, J=7.5 Hz, J=6.6 Hz, 32H), 4.5 (dt, J=8.1 Hz, J=6.6 Hz, 16H), 4.8 (dt, J=8.7 Hz, J=6.0 Hz, 16H), 8.4 (s, 16H); LD-MS obsd 3212.0, 3172.6, 3102.2, 3002.6; 3214.13 calcd (C$_{192}$H$_{288}$N$_{16}$O$_{16}$Ce); $\lambda_{abs}$ 358, 472, 644, 697 nm.

Exemplary Procedure for the Synthesis of a Cerium-Containing Triple Decker, Given for (TTP)Ce(tBPc)Ce(TTP).

A solution of CeI[N(SiMe$_3$)$_2$]$_2$ was prepared in situ by reaction of CeI$_3$ (114 mg, 0.219 mmol) and LiN(SiMe$_3$)$_2$ (438 μL, 0.438 mmol, 1M in THF) in bis(2-methoxyethyl) ether (6 mL) following the standard procedure. Then a sample of meso-tetra-p-tolylporphyrin (36.7 mg, 0.054 mmol) was added and the mixture was refluxed for 3 h, affording the metalated porphyrin as determined by UV-Vis. A sample of tBPcLi$_2$ (19.9 mg, 0.027 mmol) was added and the mixture was refluxed for 18 h. The mixture was cooled and concentrated. Chromatography (silica, CHCl$_3$/methanol 10:1) gave one band (green) which was further separated by SEC (THF). The first brownish-green band was collected and gave 12 mg after removal of the solvent. This material was suspended in methanol and filtered. The filtered material was taken up in CH$_2$Cl$_2$ and passed over a glass fiber filter. The filtrate was concentrated to give a brownish-green solid (8.6 mg, 14%). $^1$H NMR δ −2.6−−2.5 (m, 8H), −2.4−−2.3 (m, 36H), −2.1−−1.8 (m, 8H), 1.0 (s, 24H), 1.9–2.0 (m, 4H), 2.8 (m, 16H), 3.2 (m, 8H), 6.9 (m, 8H), 10.2 (m, 8H); LD-MS (POPOP) obsd 2355.3, 1545.8, 808.5, 673.4; FAB-MS obsd 2352.69, calcd 2352.80 (C$_{144}$H$_{120}$N$_{16}$Ce$_2$); $\lambda_{abs}$ 362, 422, 492, 607 nm. The second band from SEC gave the greenish double decker (TTP)Ce(tBPc) (17 mg, 41%).

(PnP)Ce(tBPc)Ce(PnP).

A solution of CeI[N(SiMe$_3$)$_2$]$_2$, prepared in situ by reaction of CeI$_3$ (182 mg, 0.349 mmol) and LiN(SiMe$_3$)$_2$ (698 μL, 0.698 mmol, 1M in THF) in bis(2-methoxyethyl) ether (5 mL) following the standard procedure, was reacted with meso-tetrapentylporphyrin (30.4 mg, 51.5 μmol) at reflux for 3 h, affording the metalated porphyrin as determined by UV-Vis. A sample of tBPcLi$_2$ (13.7 mg, 18.2 μmol) was added and the mixture was refluxed for 18 h. The mixture was cooled and concentrated. Chromatography [silica, CHCl$_3$ then CHCl$_3$/methanol (10:1)] afforded one band (green) which was further separated by SEC (THF). The first brownish-green band was collected and further purified by chromatography (silica, toluene) which afforded a brownish-green solid (7.2 mg, 13%). $^1$H NMR 6–4.3 (brs, 16H), −2.2−−2.0 (m, 8H), −2.0−−1.8 (m, 36H), 0.6 (brs, 16H), 0.8–1.0 (m, 24H), 1.1–1.2 (m, 16H), 2.2 (s, 4H), 3.6 (brs, 16H), 3.7 (brs, 16H); LD-MS (POPOP) obsd 2255.4, 2241.4, 2199.7, 2142.2, 2128.8, 1496.2; FAB-MS obsd 2193.05, calcd 2193.05 (C$_{128}$H$_{152}$N$_{16}$Ce$_2$); $\lambda_{abs}$ 354, 426, 497, 568, 615 nm. The second band from SEC afforded the greenish double decker (PnP)Ce(tBPc) (12 mg, 43%).

(TTP)Ce(tBPc)Eu(tBPc).

A solution of CeI[N(SiMe$_3$)$_2$]$_2$, prepared in situ by reaction of CeI$_3$ (106 mg, 0.204 mmol) and LiN(SiMe$_3$)$_2$ (408 μL, 0.408 mmol, 1M in THF) in bis(2-methoxyethyl) ether (5 mL) following the standard procedure, was reacted with meso-tetra-p-tolylporphyrin (12.9 mg, 19.2 μmol) at reflux for 3 h, affording the metalated porphyrin as determined by UV-Vis. The double-decker complex (tBPc)Eu(tBPc) (31.3 mg, 19.2 μmol) was added and the mixture was refluxed for 18 h. The mixture was cooled and concentrated. Chromatography [silica, CHCl$_3$ then CHCl$_3$/methanol (10:1)] gave one band (green) which was further separated twice by SEC (THF). The product was dissolved in CH$_2$Cl$_2$ and filtered over a glass fiber filter. The filtrate was concentrated, affording a bluish-green solid (24.8 mg, 55%). A $^1$H NMR spectrum was collected but the mixture of regioisomers made interpretation difficult. LD-MS obsd 2438.1, 2424.0, 1629.0, 1549.4, 809.2; FAB-MS obsd 2433.92, calcd 2433.92 (C$_{144}$H$_{134}$N$_{20}$CeEu); $\lambda_{abs}$ 346, 421, 534, 624, 714 nm.

(OEP)Ce(tBPc)Eu(tBPc).

A solution of CeI[N(SiMe$_3$)$_2$]$_2$, prepared in situ by reaction of CeI$_3$ (69.5 mg, 0.133 mmol) and LiN(SiMe$_3$)$_2$ (267 μL, 0.267 mmol, 1M in THF) in bis(2-methoxyethyl) ether (4 mL) following the standard procedure, was reacted with octaethylporphyrin (11.7 mg, 21.9 µmol) at reflux for 2.5 h, affording the metalated porphyrin as determined by UV-Vis. The double-decker complex (tBPc)Eu(tBPc) (36.0 mg, 22.1 µmol) was added and the mixture was refluxed for 18 h. The mixture was cooled and concentrated. Chromatography [silica, CHCl$_3$ then CHCl$_3$/ethyl acetate (4:1)] gave a first (red, OEPH$_2$) and a second [green, (tBPc)Eu(tBPc)] band which were not collected. The third band (blue) was further separated by SEC (THF), affording a blue solid (19.3 mg, 38%). A $^1$H NMR spectrum was collected but the mixture of regioisomers made interpretation difficult. LD-MS obsd 2298.2, 1626.8, 1408.6, 670.8; FAB-MS obsd 2297.56, 2297.98 calcd (C$_{132}$H$_{140}$N$_{20}$CeEu); $\lambda_{abs}$ 344, 400, 546, 628, 712 nm.

(TTP)Ce[(octyloxy)$_8$Pc]Eu[(octyloxy)$_8$Pc].

A solution of CeI[N(SiMe$_3$)$_2$]$_2$, prepared in situ by reaction of CeI$_3$ (53.1 mg, 0.102 mmol) and LiN(SiMe$_3$)$_2$ (204 µL, 0.204 mmol, 1M in THF) in bis(2-methoxyethyl) ether (4 mL) following the standard procedure, was reacted with meso-tetra-p-tolylporphyrin (17.1 mg, 25.5 µmol) at reflux for 3 h, affording the metalated porphyrin as determined by UV-Vis. The double-decker complex [(octyloxy)$_8$Pc]Eu[(octyloxy)$_8$Pc] (29.8 mg, 9.2 µmol) was added and the mixture was refluxed for 24 h. The mixture was cooled and concentrated. Chromatography [silica, hexane/ether (9:1) then hexane/ether (4:1)] gave a first (red, TTPH$_2$) and a second (brown, reduced form of the double decker) band which were not collected. The third band (brown-green) was further separated by SEC (THF), the second band (green) was collected and further purified by chromatography [silica, hexane/ether (9:1)] affording an olive-green solid (14.5 mg, 39%). $^1$H NMR δ 0.72 (t, J=7.2 Hz, 24H), 0.8–1.0 (m, 32H), 0.99 (t, J=7.2 Hz, 24H), 1.0–1.4 (m, 76H), 1.4–1.5 (m, 32H), 1.5–1.7 (m, 32H), 1.7–1.9 (m, 16H), 2.0–2.2 (m, 16H), 2.5–2.6 (m, 8H), 3.5–3.6 (m, 8H), 5.0–5.1 (m, 16H), 5.3–5.4 (m, 8H), 5.4–5.5 (m, 8H), 5.9–6.0 (m, 8H), 6.42 (brs, 8H), 11.19 (s, 8H); LD-MS obsd 4038.4, 3828.3, 807.8; calcd avg mass 4037.4 (C$_{240}$H$_{324}$N$_{20}$O$_{16}$CeEu); $\lambda_{abs}$ 371, 426, 538, 629, 669, 721 nm.

(PnP)Ce(tBPc)Eu(TTP).

A solution of CeI[N(SiMe$_3$)$_2$]$_2$, prepared in situ by reaction of CeI$_3$ (105 mg, 0.202 mmol) and LiN(SiMe$_3$)$_2$ (404 µL, 0.404 mmol, 1M in THF) in bis(2-methoxyethyl) ether (5 mL) following the standard procedure, was reacted with meso-tetrapentylporphyrin (11.7 mg, 19.8 µmol) at reflux for 3 h, affording the metalated porphyrin as determined by UV-Vis. The double-decker complex (TTP)Eu(tBPc) (29.0 mg, 18.8 µmol) was added and the mixture was refluxed for 3.5 h. The mixture was cooled and concentrated. Chromatography [silica, CHCl$_3$ then CHCl$_3$/methanol (10:1)] gave one band (green), which was further separated by SEC (THF). The first band (brownish-green) was further chromatographed (silica, CHCl$_3$). The product was dissolved in CH$_2$Cl$_2$ and filtered over a glass fiber filter. The filtrate was concentrated, affording a brownish-green solid (24.2 mg, 57%). $^1$H NMR δ −0.7−−0.5 (brs, 8H), 0–0.1 (m, 12H), 0.1–0.3 (m, 16H), 0.3–0.5 (m, 8H), 0.5–0.7 (m, 36H), 1.5 (s, 4H), 2.9 (s, 12H), 5.0–5.5 (m, 8H), 6.3–6.7 (m, 8H), 7.0–7.2 (m, 8H), 8.0 (s, 4H), 8.1 (d, 4H), 9.1 (d, 4H), 12.5 (brs, 4H), 13.3 (brs, 4H); LD-MS (POPOP) obsd 2284.3, 2226.3, 2212.8, 2158.3; FAB-MS obsd 2285.92, calcd 2285.94 (C$_{136}$H$_{140}$N$_{16}$CeEu); $\lambda_{abs}$ 360, 367, 421, 493, 607 nm.

(3-Por)Ce(tBPc)Eu(TTP).

A solution of CeI[N(SiMe$_3$)$_2$]$_2$, prepared in situ by reaction of CeI$_3$ (125 mg, 0.240 mmol) and LiN(SiMe$_3$)$_2$ (481 µL, 0.481 mmol, 1M in THF) in bis(2-methoxyethyl) ether (5 mL) following the standard procedure, was reacted with 3-PorH$_2$ (41.4 mg, 47.9 µmol) at reflux for 3 h, affording the metalated porphyrin as determined by UV-Vis. The double-decker complex (TTP)Eu(tBPc) (74.8 mg, 48.1 µmol) was added and the mixture was refluxed for 18 h. The mixture was cooled and concentrated. Chromatography [silica, CHCl$_3$ then CHCl$_3$/methanol (10:1)] gave one band (green), which was further separated thrice by SEC (THF), affording a brownish-green solid (44.2 mg, 36%). A $^1$H NMR spectrum was collected but the mixture of regioisomers made interpretation difficult. LD-MS obsd 2548.3, 2424.5; FAB-MS obsd 2559.72, calcd 2559.72 (C$_{147}$H$_{123}$CeEuIN$_{16}$Si); $\lambda_{abs}$ 364, 420, 493, 607 µm.

The foregoing is illustrative of the present invention, and is not to be construed as limiting thereof. The invention is defined by the following claims, with equivalents of the claims to be included therein.

That which is claimed is:

1. A half-sandwich coordination complex, useful for the synthesis of triple-decker sandwich coordination compounds, produced by the process of:

reacting a precursor complex of the formula XM(R$^1$)$_2$ with a free base porphyrinic macrocycle to produce said half-sandwich complex;

wherein X is a halogen,

M is a metal selected from the group consisting of Ce, Pr, Nd, Sm, Eu, Gd, Tb, Dy, Ho, Er, Tm, Yb and Lu, and R$^1$ is an amide.

2. The half-sandwich coordination complex of claim 1, wherein M is selected from the group consisting of Ce, Pr, Nd, Sm, and Eu.

3. The half-sandwich coordination complex of claim 1, wherein M is selected from the group consisting of Ce and Eu.

4. The half-sandwich coordination complex of claim 1, wherein X is selected from the group consisting of Cl and I.

5. The half-sandwich coordination complex of claim 1, wherein X is Cl.

6. The half-sandwich coordination complex of claim 1, wherein R$^1$ is an amide of the formula —NR$^2$R$^3$, wherein R$^2$ and R$^3$ are each independently selected from the group consisting of C1–C6 alkyl and silyl.

7. The half-sandwich coordination complex of claim 1, wherein R$^1$ is a disilylamide.

8. The half-sandwich coordination complex of claim 1, wherein R$^1$ is a disilylamide of the formula —N(SiMe$_3$)$_2$.

9. The half sandwich coordination complex of claim 1, wherein said free base porphyrinic macrocycle is selected from the group consisting of compounds of Formula X and compounds of Formula XI:

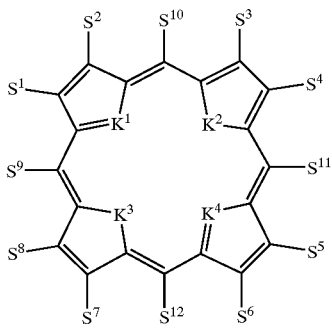

(X)

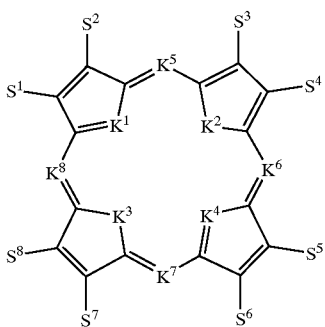

(XI)

wherein:
- $K^1$, $K^2$, $K^3$, $K^4$, $K^5$, $K^6$, $K^7$, and $K^8$ are independently selected from the group consisting of N, O, S, Se, and Te;
- $S^1$, $S^2$, $S^3$, $S^4$ $S^5$, $S^6$, $S^7$, $S^8$, $S^9$, $S^{10}$, $S^{11}$, and $S^{12}$ are independently selected substituents each selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
- and wherein each pair of $S^1$ and $S^2$, $S^3$ and $S^4$, $S^5$ and $S^6$, and $S^7$ and $S^8$, may independently form an annulated arene selected from the group consisting of benzene, naphthalene, and anthracene, which annulated arene may in turn may be unsubstituted or substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

10. A half sandwich coordination complex according to claim 9, wherein:
M is selected from the group consisting of Ce and Eu;
X is selected from the group consisting of Cl and I; and
R is a disilylamide.

11. A half-sandwich coordination complex, useful for the synthesis of triple-decker sandwich coordination compounds, according to Formula (I):

L-M-X      (I)

wherein:
X is a halogen;
M is a metal selected from the group consisting of Ce, Pr, Nd, Sm, Eu, Gd, Tb, Dy, Ho, Er, Tm, Yb and Lu, and
L is a porphyrinic macrocycle group.

12. The half-sandwich coordination complex of claim 11, wherein M is selected from the group consisting of Ce, Pr, Nd, Sm, and Eu.

13. The half-sandwich coordination complex of claim 11, wherein M is selected from the group consisting of Ce and Eu.

14. The half-sandwich coordination complex of claim 11, wherein X is selected from the group consisting of Cl and I.

15. The half-sandwich coordination complex of claim 11, wherein X is Cl.

16. The half sandwich coordination complex of claim 11, wherein said porphyrinic macrocycle is selected from the group consisting of compounds of Formula X and compounds of Formula XI:

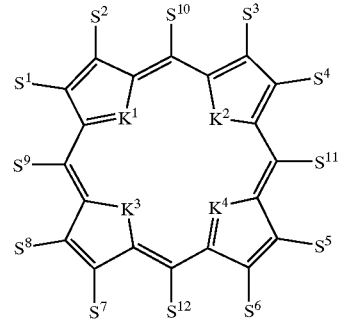

(X)

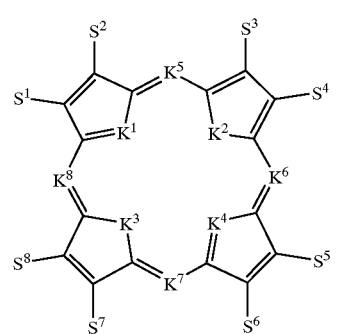

(XI)

wherein
- $K^1$, $K^2$, $K^3$, $K^4$, $K^5$, $K^6$, $K^7$, and $K^8$ are independently selected from the group consisting of N, O, S, Se, and Te;
- $S^1$, $S^2$, $S^3$, $S^4$ $S^5$, $S^6$, $S^7$, $S^8$, $S^9$, $S^{10}$, $S^{11}$, and $S^{12}$ are independently selected substituents each selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
- and wherein each pair of $S^1$ and $S^2$, $S^3$ and $S^4$, $S^5$ and $S^6$, and $S^7$ and $S^8$, may independently form an annulated arene selected from the group consisting of benzene, naphthalene, and anthracene, which annulated arene may in turn may be unsubstituted or substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

17. A half sandwich coordination complex according to claim 16, wherein:
M is selected from the group consisting of Ce and Eu; and
X is selected from the group consisting of Cl and I.

18. A method of making a half sandwich coordination complex, comprising the steps of:

reacting a precursor complex of the formula $X\text{-}M(R^1)_2$, with a free base porphyrinic macrocycle to produce said half-sandwich complex;

wherein X is a halogen,

M is a metal selected from the group consisting of Ce, Pr, Nd, Sm, Eu, Gd, Tb, Dy, Ho, Er, Tm, Yb and Lu, and $R^1$ is an amide.

19. The method according to claim 18, wherein said reacting step is carried out in a nonaqueous solvent.

20. The method according to claim 18, wherein said reacting step is carried out in a polar aprotic organic solvent.

21. A method according to claim 18, wherein said reacting step is carried out in a glyme solvent.

22. The method according to claim 18, wherein said reacting step is carried out at a temperature of 200° C. or less.

23. The method according to claim 18, wherein said reacting step is carried out at a temperature of from 100° C. to 200° C.

24. The method according to claim 18, wherein M is selected from the group consisting of Ce, Pr, Nd, Sm, and Eu.

25. The method according to claim 18, wherein X is selected from the group consisting of Cl and I.

26. The method according to claim 18, wherein X is Cl.

27. The method according to claim 18, wherein $R^1$ is an amide of the formula $-NR^2R^3$, wherein $R^2$ and $R^3$ are each independently selected from the group consisting of C1–C6 alkyl and silyl.

28. A method according to claim 18, wherein said precursor complex is produced by the steps of:

reacting a compound of the formula $MX_3$, wherein M is a lanthanide metal and X is halogen, with a compound of the formula $ZR^1$, wherein Z is a counter-ion and $R^1$ is an amide, to produce said precursor complex of the formula $X\text{-}M(R^1)_2$.

29. A method of making a triple-decker sandwich coordination compound, comprising the steps of:

reacting a half-sandwich coordination complex according to claim 1 or 11 with a double-decker sandwich coordination compound in a polar aprotic solvent at a temperature of at least 100° C. to produce said triple-decker sandwich coordination compound.

30. A method according to claim 29, wherein said double-decker sandwich coordination compound is a heteroleptic sandwich coordination compound.

31. The method according to claim 29, wherein said double-decker sandwich coordination compound is a homoleptic sandwich coordination compound.

* * * * *

UNITED STATES PATENT AND TRADEMARK OFFICE
CERTIFICATE OF CORRECTION

PATENT NO.    : 6,642,376 B2
DATED         : November 4, 2003
INVENTOR(S)   : Lindsey et al.

It is certified that error appears in the above-identified patent and that said Letters Patent is hereby corrected as shown below:

Column 38,
Line 24, should read -- $\lambda_{abs}$ 364, 420, 493, 607 nm. --

Column 39,
Line 66, should read -- Nd, Sm, Eu, Gd, Tb, Dy, Ho, Er, Tm, Yb and Lu, and --

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,642,376 B2 | Page 1 of 1 |
| APPLICATION NO. | : 10/135220 | |
| DATED | : November 4, 2003 | |
| INVENTOR(S) | : Lindsey et al. | |

It is certified that error appears in the above-identified patent and that said Letters Patent is hereby corrected as shown below:

In The Specification

Column 1, Line 11: Please insert the following as a separate paragraph

--This invention was made with government support under grant number N00014-99-1-0357 awarded by the Office of Naval Research. The government has certain rights to this invention.--

Signed and Sealed this
Twenty-eighth Day of July, 2015

Michelle K. Lee
*Director of the United States Patent and Trademark Office*